(12) United States Patent
Wang et al.

(10) Patent No.: US 12,410,686 B2
(45) Date of Patent: Sep. 9, 2025

(54) MONITORING SCALE INHIBITOR TREATMENT

(71) Applicant: Saudi Arabian Oil Company, Dhahran (SA)

(72) Inventors: Qiwei Wang, Dhahran (SA); Tao Chen, Dhahran (SA); Hameed H. Al-Badairy, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 715 days.

(21) Appl. No.: 17/708,802

(22) Filed: Mar. 30, 2022

(65) Prior Publication Data
US 2023/0313644 A1 Oct. 5, 2023

(51) Int. Cl.
| | |
|---|---|
| E21B 37/06 | (2006.01) |
| C09K 8/528 | (2006.01) |
| E21B 43/20 | (2006.01) |
| G01N 23/20091 | (2018.01) |
| G01N 33/18 | (2006.01) |
| H01J 37/28 | (2006.01) |
| G01N 1/40 | (2006.01) |

(52) U.S. Cl.
CPC .............. *E21B 37/06* (2013.01); *C09K 8/528* (2013.01); *E21B 43/20* (2013.01); *G01N 23/20091* (2013.01); *G01N 33/1853* (2013.01); *H01J 37/28* (2013.01); *G01N 1/4077* (2013.01)

(58) Field of Classification Search
None
See application file for complete search history.

(56) References Cited

U.S. PATENT DOCUMENTS

| | | |
|---|---|---|
| 3,613,788 A | 10/1971 | Kautsky |
| 6,478,971 B1 | 11/2002 | Koefod et al. |
| 6,886,406 B1 | 5/2005 | Couet et al. |
| 7,144,511 B2 | 12/2006 | Vuong |
| 7,985,318 B2 | 7/2011 | Shevchenko et al. |
| 8,303,768 B2 | 11/2012 | Shevchenko et al. |
| 9,085,477 B2 | 7/2015 | Banerjee et al. |
| 9,266,754 B2 | 2/2016 | Wahid |
| 9,612,204 B2 | 4/2017 | Locklear et al. |

(Continued)

FOREIGN PATENT DOCUMENTS

| | | |
|---|---|---|
| AU | 2009238632 | 10/2009 |
| TW | I241988 | 10/2005 |

(Continued)

OTHER PUBLICATIONS

U.S. Appl. No. 17/347,053, filed Jun. 14, 2021, AlGhunaimi et al.
(Continued)

*Primary Examiner* — Andrew Sue-Ako
(74) *Attorney, Agent, or Firm* — Fish & Richardson P.C.

(57) ABSTRACT

A method and system of treatment with scale inhibitor, including adding scale inhibitor to source water to give injection water, conveying the injection water in a surface conduit to an injection well for injection into an oil reservoir in a subterranean formation, pumping the injection water through a wellbore of the injection well into the oil reservoir, obtaining a sample of the injection water (including suspended solids), and analyzing the suspended solids.

25 Claims, 21 Drawing Sheets

(56) References Cited

U.S. PATENT DOCUMENTS

| | | | |
|---|---|---|---|
| 9,643,865 | B2 | 5/2017 | Matherly et al. |
| 10,501,680 | B2 | 12/2019 | Li et al. |
| 11,174,178 | B2 | 11/2021 | Hull et al. |
| 11,866,640 | B2 | 1/2024 | Wang et al. |
| 2011/0163032 | A1 | 7/2011 | Alexander et al. |
| 2012/0118575 | A1 | 5/2012 | Griffin |
| 2012/0322699 | A1 | 12/2012 | Karazincir et al. |
| 2013/0248186 | A1* | 9/2013 | Koskan .................. E21B 43/20 166/305.1 |
| 2016/0177171 | A1* | 6/2016 | Hernández Al Tamirano ............ C23F 11/173 507/224 |
| 2020/0003052 | A1* | 1/2020 | Benoit .................... E21B 49/02 |
| 2023/0331598 | A1 | 10/2023 | Wang et al. |

FOREIGN PATENT DOCUMENTS

| WO | WO 2012109313 | 8/2012 |
|---|---|---|
| WO | WO 2013131183 | 9/2013 |
| WO | WO 2015013146 | 1/2015 |

OTHER PUBLICATIONS

Al Kalbani et al., "Impact of Relaxation of LSSW Parameters on Scaling Risk," SPE-200695-MS, presented at the SPE International Oilfield Scale Conference and Exhibition, Jun. 2020, 26 pages.

Al-Riyami et al., "When Will Low Sulphate Seawater No. Longer Be Required on the Tiffany Field?" SPE International Symposium and Exhibition on Formation Damage Control held in Lafayette, Feb. 2008, 15 pages.

Al-Samhan et al., "Evaluating scale deposition and scale tendency of effluent water mix with seawater for compatible injection water," Journal of Petroleum Exploration and Production Technology, 2020, 10:2105-2111, 7 pages.

BinGhanim et al., "High Temperature Fracturing Fluid Based on Nanofiltrated Seawate," SPE-189048, presented at the SPE Kingdom of Saudi Arabia Annual Technical Symposium and Exhibition, Apr. 2017, 17 pages.

BinGhanim et al., "Scale Mitigation Strategy for Fracturing Using Seawater-Based Fluid," SPE-188029, presented at the SPE Kingdom of Saudi Arabia Annual Technical Symposium and Exhibition, Apr. 2017, 16 pages.

Collins et al., "Sulphate Removal for Barium Sulphate Scale Mitigation a Deepwater Subsea Production System," SPE-189048, presented at the SPE International Symposium on Oilfield Scale, May 2004, 11 pages.

Davis et al., "The Advancement of Sulfate Removal from Seawater in Offshore Waterflood Operations," Paper 02314, Corrosion 2002, NACE International, Apr. 2002, 13 pages.

Emmons et al., "On-Site, Near-Real-Time Monitoring of Scale Deposition," SPE 56776, presented at the SPE Annual Technical Conference and Exhibition, Oct. 1999, 6 pages.

Eseosa et al., "Prediction and Monitoring of Oilfield Carbonate Scales Using Scale Check," SPE 56776, presented at the Nigeria Annual International Conference and Exhibition, Jul.-Aug. 2011, 10 pages.

Heatherly et al., "Sulfate Removal Technology for Seawater Waterflood Injection," Offshore Technology Conference, May 1994, 18 pages.

Karadkar et al., "Elimination of Scaling Potential of Seawater in Downhole Environment through the Innovative Use of Nanofiltration and Scale Inhibitor," SPE Kingdom of Saudi Arabia Annual Technical Symposium and Exhibition, Apr. 2016, 13 pages.

Kirboga et al., "Effect of the experimental parameters on calcium carbonate precipitation," Chemical Engineering Transactions, Jun. 2013, 32:2119-2124, 7 pages.

Li et al., "A More Sustainable Approach: Nanofiltered Seawater-based High Temperature Fracturing Fluids," SPE-194708, presented at the SPE Middle East Oil and Gas Show and Conference, Mar. 2019, 14 pages.

Mackay et al., "Integrated Risk Analysis for Scale Management in Deepwater Developments," SPE Production & Facilities, May 2005, 20(02):138-154, 17 pages.

Mitchell et al., "Water Injection Methods," SPE 10028, International Petroleum Exhibition and Technical Symposium, Mar. 1982, 16 pages.

Monroe et al., "Gravel Packing High-Volume Water Supply Wells," Journal of Petroleum Technology, Dec. 1980, 32(12):2097-2102, 6 pages.

Moore et al., "Treatments to Improve the Performance of Injection, Disposal and Water Supply Wells," Journal of Petroleum Technology, Sep. 1959, 11(09):37-41, 5 pages.

Muresan et al., "Adsorption and surface-induced precipitation of poly(acrylic acid) on calcite revealed with atomic force microscopy," Colloids and Surfaces A: Physicochemical and Engineering Aspects, Oct. 2011, 390(1-3):225-230, 6 pages.

Muryanto et al., "Effects of malonic acid on calcium carbonate crystalline phases and morphology," Proceedings of the International Conference on Science and Technology: Atlantis Highlights in Engineering, Dec. 2018, 6 pages.

Nasr-El-Din et al., "Simulation of Injection Water Supply Wells in Central Arabia," Abu Dhabi International Petroleum Exhibition and Conference, Oct. 1996, 20 pages.

Nasr-El-Din, "New Mechanisms of Formation Damage: Lab Studies and Case Histories," SPE European Formation Damage Conference, May 2003, 12 pages.

Ostroff, "Injection Water Problems Identified by Laboratory Analysis," Middle East Technical Conference and Exhibition, Mar. 1981, 10 pages.

Pedenaud et al., "Industrial Experience in Sea Water Desulfation," SPE 10028, presented at the SPE International Conference and Exhibition on Oilfield Scale, May 2012, 8 pages.

Scott, "Pilot Testing of Membrane Technology to Selectively Remove Sulfate Ion From Seawater in the Wilmington Field," SPE 25152, presented at the SPE International Symposium on Oilfield Chemistry, Mar. 1993, 10 pages.

Seland et al., "Membrane Filtration of Seawater for Oil Reservoir Injection," SPE 24805, presented at the SPE Annual Technical Conference and Exhibition, Oct. 1992, 12 pages.

Shen et al., "Seawater injection, inhibitor transport and rock-brine interactions," SPE 114062, presented at the SPE International Oilfield Scale Conference, May 2008, 14 pages.

Vu et al., "Eliminating the Need for Scale Inhibition Treatments for Elf Exploration Angola's Girassol Field," SPE 60220, presented at the International Symposium on Oilfield Scale, Jan. 2000, 10 pages.

Wang et al., "CaCO3 scale prevention by additives in the presence of heavy metal ions," International Journal of Corrosion and Scale Inhibition, 2016, 5(1):12-30, 20 pages.

Wang et al., "Laboratory Study on Efficiency of Three Calcium Carbonate Scale Inhibitors in The Presence of EOR Chemicals," Petroleum, Dec. 2018, 4(4):375-384, 10 pages.

Xyla et al., "The inhibition of Calcium carbonate precipitation in Aqueous media by organophosphorus compounds," Journal of Colloid Interface and Science, Oct. 1992, 153(2):537-551, 15 pages.

Yang et al., "Investigation of Calcium Carbonate Scaling Inhibition and Scale Morphology by AFM," J Colloid Interface Sci., Aug. 2001, 240(2):608-621, 14 pages.

Zhang et al., "Investigation of scale inhibition mechanisms based on the effect of scale inhibitor on calcium carbonate crystal forms," Science in China Series B: Chemistry, Feb. 2007, 50(1):114-120, 7 pages.

* cited by examiner

MONITORING SCALE INHIBITOR TREATMENT

TECHNICAL FIELD

This disclosure relates to scale inhibition in the supply of water for injection.

BACKGROUND

An application for water is injection into oil-producing formations to enhance (increased) oil production. Water injection or water flooding may be water injected into an oil reservoir to maintain reservoir pressure or to drive oil towards production wells. Water injection wells may be located onshore or offshore to increase oil recovery from an existing reservoir. Produced water, aquifer water, and surface water (e.g., seawater) may be a source of bulk water utilized for injection for recovery of oil. Produced water can be water produced along with hydrocarbon from a subterranean formation. Aquifer water may be from water-bearing formations other than a hydrocarbon reservoir. The water-bearing formation can be in the same structure as a hydrocarbon reservoir.

SUMMARY

An aspect relates to a method of treatment with scale inhibitor, including adding scale inhibitor to source water to give injection water, conveying the injection water in a surface conduit to an injection well for injection into an oil reservoir in a subterranean formation, pumping the injection water through a wellbore of the injection well into the oil reservoir, obtaining a sample of the injection water (including suspended solids), and analyzing the suspended solids via energy dispersive x-ray spectroscopy (EDS), x-ray diffraction (XRD), or x-ray fluorescence (XRF), or any combinations thereof.

Another aspect relates to a method of treatment with scale inhibitor, including adding scale inhibitor to source water to give injection water for injection via an injection well into an oil reservoir having crude oil. The method includes obtaining a sample of the injection water (having suspended solids), analyzing the suspended solids via EDS, XRD, or XRF, or any combinations thereof, thereby identifying calcium carbonate solids of the suspended solids, and analyzing the calcium carbonate solids via imaging, thereby identifying at least some of the calcium carbonate solids as formed in presence of the scale inhibitor.

Yet another aspect relates to a method of treatment with scale inhibitor, including adding scale inhibitor to source water to give injection water for injection via an injection well into an oil reservoir, and conveying the injection water in a surface conduit to the injection well for injection into the oil reservoir. The method includes obtaining a sample of the injection water (having suspended solids), analyzing the suspended solids via EDS, thereby identifying calcium carbonate solids of the suspended solids, and analyzing the calcium carbonate solids via scanning electron microscopy (SEM) or environmental scanning electron microscopy (ESEM), or both, thereby identifying at least some of the calcium carbonate solids as formed in presence of the scale inhibitor. The method includes increasing an amount of the scale inhibitor added to the source water in response to identifying at least some of the calcium carbonate solids as formed in the presence of the scale inhibitor.

The details of one or more implementations are set forth in the accompanying drawings and the description below. Other features and advantages will be apparent from the description and drawings, and from the claims.

BRIEF DESCRIPTION OF DRAWINGS

Like reference numbers and designations in the various drawings indicate like elements.

DETAILED DESCRIPTION

Figure 1:
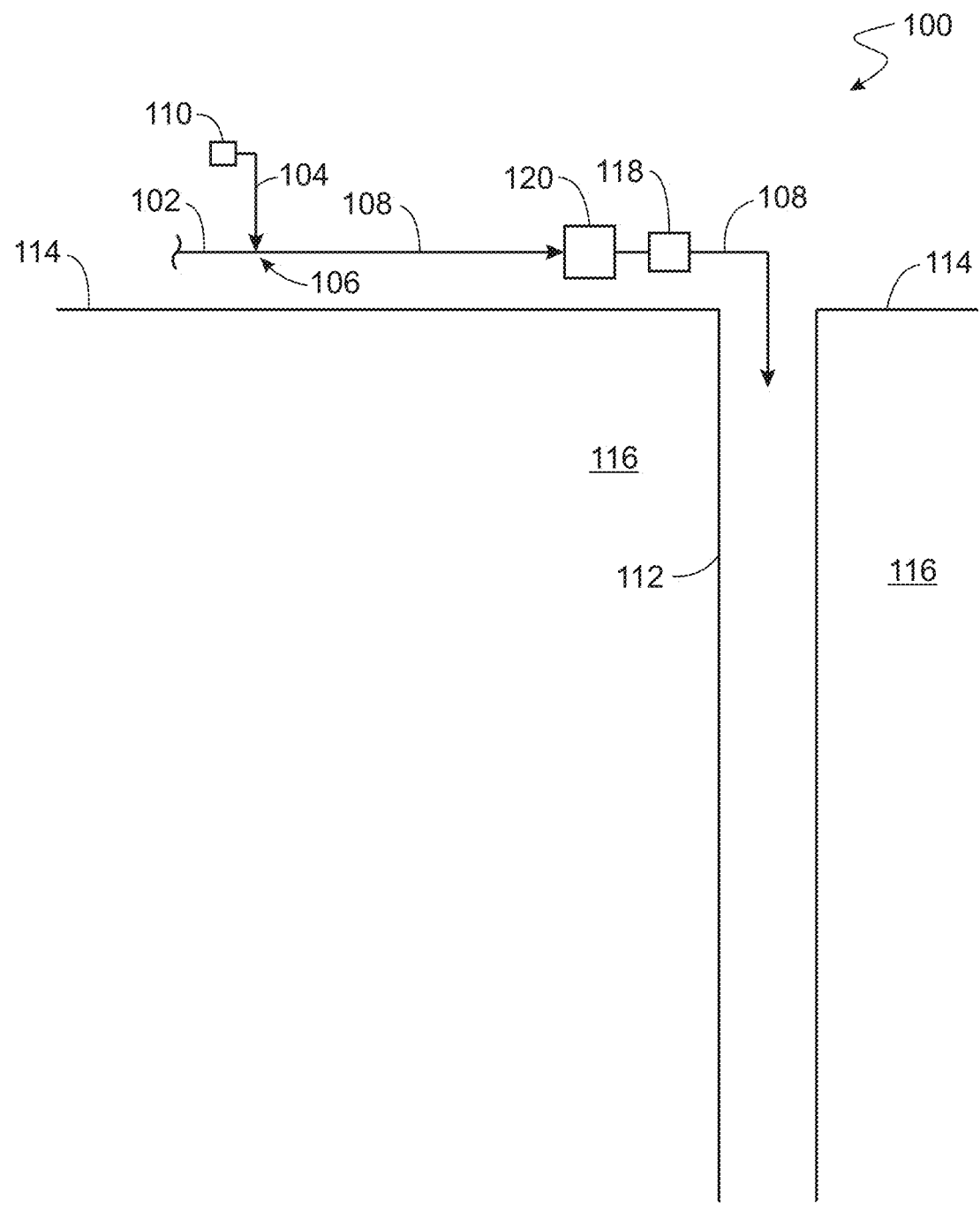
FIG. 1 is a diagram of an injection well.

Some aspects of the present disclosure are directed to identifying the sources of calcium carbonate solids in injection water systems. Embodiments may differentiate the root cause of calcium carbonate solids in injection water systems. The approach may offer information to assess if the scale-inhibitor treatment program is effective. If treatment program is ineffective, calcium carbonate can precipitate from the injection water and accumulate at the bottom of water lines, which can cause severe under-deposit corrosion and deteriorate the asset integrity.

Embodiments may utilize a first technique [e.g., energy dispersive x-ray spectroscopy (EDS)] to identify calcium carbonate. Then, utilizing a second technique [e.g., environmental scanning electron microscopy (ESEM) or scanning electron microscopy (SEM)], the source of calcium carbonate ($CaCO_3$) may be determined (e.g., based on morphology of the calcium carbonate). ESEM can be characterized as a form of SEM. For an effective scale treatment program, the suspended solids or solids recovered during scrapping should generally be free of calcium carbonate that was formed in the presence of the scale inhibitor.

Embodiments may relate to assessing the efficacy of $CaCO_3$-scale inhibition treatment in preventing formation of $CaCO_3$ in water for injection. Solids collected from the water (and from scraping/pigging operations) may be analyzed to determine if any of the collected solids are $CaCO_3$ formed downstream of the scale-inhibitor injection point in the water supply system. The analysis (assessment) may include: (1) collected solids are analyzed to determine if $CaCO_3$ solids are present; (2) if $CaCO_3$ solids are not present, the $CaCO_3$-scale inhibition treatment is deemed effective; and (3) if $CaCO_3$ solids are present, the collected $CaCO_3$ solids are analyzed via ESEM or SEM imaging (for size, shape and surface morphology) to determine if any of these collected $CaCO_3$ solids were formed in the presence of the scale inhibitor. Advantages of ESEM may be that ESEM can operate with the samples being wet, or in low vacuum or gas, and ESEM may be especially applicable for uncoated calcium carbonate. Both ESEM and SEM can be utilized to evaluate if collected $CaCO_3$ solids were formed in the presence of the scale inhibitor. If any of the collected $CaCO_3$ solids are determined as formed in the presence of the scale inhibitor, the addition amount or rate of the scale inhibitor introduced at the injection point may be increased in response.

In examples below, calcium carbonate scale tests with and without scale inhibitors were performed. EDS and ESEM analyses were conducted. Experiments were carried out to differentiate the differences in morphologies of calcium carbonate suspended solids or scales to determine the origin (source) of the calcium carbonate.

Formation of calcium carbonate scale may be a problem in systems handling and supplying water for injection. Formation of scale deposits can have a significant impact on operation. Scale inhibitors are chemicals that may be utilized to control (reduce, prevent) the scale formation. Monitoring may be beneficial to assess that the treatment is sufficient. Conventional monitoring methods, such as scale-inhibitor residual concentration, water chemistry (composition) analysis, and utilization of scale coupons, can be inadequate. Other techniques, such as measuring total suspended solids in the water including via on-line instruments may be problematic in the difficulty to distinguish between particles (e.g., scale particles) formed after the scale-inhibitor injection point versus particles are already present in water stream prior to the scale inhibitor injection.

As discussed, in embodiments herein may assess the efficiency of a scale-inhibition treatment program to prevent calcium carbonate scaling in a water injection system or water supply system for injection. Suspended solids may be collected from the water stream flowing to the injection well, and/or solid deposits may be recovered from scraping and pigging operations of water conduits (piping). These solids may be characterized by EDS and SEM (or ESEM in particular). EDS analysis can distinguish calcium carbonate solids in the analyzed solid samples from other types of inorganic minerals, such as dolomite, calcium sulfate, barium sulfate, quartz, clays, iron sulfides, etc. In implementations, inorganic compounds (minerals or solids) (e.g., calcium sulfate, barium sulfate, iron sulfide, etc.) other than calcium carbonate solids can contribute to scale formation. These other solids may be considered. A focus of certain embodiments is calcium carbonate solids.

With the calcium carbonate solids identified via EDS, the ESEM or SEM analysis can then distinguish between calcium carbonate particles (scale particles) formed in presence of the scale inhibitor versus calcium carbonate particles sourced upstream of the scale-inhibitor injection point. The calcium carbonate particles from upstream of the scale-inhibitor injection point may be calcium carbonate particles that formed upstream of the scale-inhibitor injection point, calcium carbonate particles originating from drilling cuts of limestone rocks, and/or calcium carbonate particles utilized in drilling muds or completion fluids as a bridging agent and/or weighting agent (weighting material). The determining of the source of the calcium carbonate particles in the collected solids via SEM (which may include ESEM) may be based on the calcium-carbonate shapes and surface morphologies. With effective chemical treatment, no calcium carbonate scale particles will generally be formed after (downstream) of the scale-inhibitor chemical injection point.

Embodiments of the present techniques can determine if the chemical treatment program is effective for calcium carbonate scale prevention. The present techniques may be superior to other scale monitoring methods by providing relatively reliable results for injection water systems with respect to monitoring scale prevention via a scale inhibitor. Therefore, embodiments may improve or optimize the scale-inhibition treatment program for increasing or maximizing protection of system integrity. The present monitoring may instruct to increase the amount of scale inhibitor. The present monitoring may instruct that the amount of scale inhibitor can be reduced, thus reducing or minimizing the chemical cost.

Formation of calcium carbonate scale is a common problem in oilfield operations. Water injection is widely applied in the oil industry to increase reservoir pressure and/or to sweep crude oil from the reservoir and push the oil towards a production well, thereby increasing hydrocarbon production and maintaining the production rate of a reservoir over a longer period. Aquifer water, surface water (e.g., seawater), and/or produced water may be the injection water (the water injected via an injection well into an oil reservoir). Aquifer water may be from water-bearing formations (e.g., an aquifer in a subterranean formation) and brought to surface via a water well (water supply well). Produced water can be water produced along with hydrocarbon from a subterranean formation. The produced water can be separated from the produced hydrocarbon (e.g., crude oil and/or natural gas) and utilized as injection water. The produced water may be separated from the hydrocarbon at or adjacent a wellhead (via separation equipment), or at a gas oil separation plant (GOSP), and the like.

Aquifer water is one of the main sources of water for injection of both inland and offshore oil fields, especially when other waters are unavailable or unsuitable.

Seawater may be problematic as injection water because formation waters in some oil-bearing reservoirs (that receive the injected water) contain relatively high amounts of divalent cations, such as calcium, strontium and barium. Therefore, if seawater is injected, the sulfate ions in seawater will generally react with the divalent cations in the formation water to form scale precipitates. The precipitates can deposit in the reservoir, wellbore, downhole tubular, and surface equipment. Such may be detrimental to the efficiency of the oil recovery process blocking fluid flow and interference with operation. Removal of sulfate ions from seawater is a relatively costly process. Thus, aquifer water may be typically be utilized as injection water even where seawater is available.

Produced water is often reinjected, but the volumes of produced water being produced are commonly insufficient. Thus, if produced water is injected, an additional water source may be provided for injection. Aquifer water can be that additional water.

Aquifer water (whether as a sole source or additional source of injection water) may be transported through surface piping (conduit) to the injection well. The formation of calcium carbonate scale precipitation in the surface transfer piping and other equipment associated with piping and surface transfer. In some implementations, the aquifer may be transported over a relatively long distance through the piping to reach the injection well(s), which can result in increased formation of calcium carbonate scale precipitation.

Aquifer waters generally contain dissolved carbon dioxide gas, which may keep (maintain) the water at equilibrium with respect to dissolved calcium carbonate solubility, or even slightly below the calcium carbonate solubility under aquifer reservoir conditions. As the aquifer water is brought up to surface and transported in surface piping (pipe, conduit, flowline), turbulent flow and pressure change (drop, decrease) to a lower pressure can lead to loss of dissolved carbon dioxide gas in the aquifer water. As this occurs, the water pH may increase and the water may become supersaturated to calcium carbonate, and therefore calcium carbonate may precipitate out from the water.

The precipitated calcium carbonate particles could either attached to the pipe surface or stay suspended and flow with the water stream. The calcium carbonate particles staying suspended and flowing with the water may be more harmful to water injection operation than if the calcium carbonate particles attached to the piping. First, the calcium carbonate particles can plug the injection wells and reduce the water injection rate. Second, the calcium carbonate particles can accumulate on the bottom of the pipe (flowline) and form sludge. Such can cause under-deposit corrosion and result in rupturing of the pipe. This may be particularly significant for long distance piping and/or low water flowrates in the pipe (flowline).

Formation of calcium carbonate can be controlled with the use of chemical additives called antiscalants or scale inhibitors. These additives (scale inhibitors) are commonly organic phosphates or polyacrylate based polymeric compound. These chemicals (scale inhibitors) may be applied to the injection water by [1] continuous injection (e.g., by a metering pump) into surface equipment or piping conveying the injection water, [2] by periodically squeezing the scale inhibitor chemical composition into the aquifer reservoir, and/or [3] by pumping (e.g., continuous injection) the scale inhibitor product down the backside of the water supply well. The performance of the scale-inhibitor treatment generally should be monitored to confirm the treatment is effective.

An industry standard for monitoring the performance of a scale-inhibitor treatment program typically relies on determining (measuring) inhibitor concentration in the water as conveyed in the surface pipe (flowline), and comparing the measured concentration to a pre-determined critical inhibitor concentration. The critical inhibitor concentration can be at or above a minimum effective dose (MED) in which calcium carbonate formation is prevented. MED can also be labeled as minimum inhibitory concentration (MIC).

First, a problem may be that the critical inhibitor concentration (MED) is estimated. In other words, the critical inhibitor concentration is predetermined in the laboratory. The laboratory testing may not resemble (and could be very different from) the actual field conditions. Therefore, the predetermined critical concentration may not be sufficient (for actual conditions) to prevent calcium carbonate formation, or may be overestimated (for actual conditions), which could lead to wasted consumption of excess scale inhibitor in implementations. Second, analysis (measurement) of scale-inhibitor concentration in the flowing water (or in samples collected from the flowing water) can be difficult at low concentration of the scale inhibitor and can be inaccurate due to interference of other impurities in water, especially for polymeric scale inhibitors. Third, changes in water composition and operation conditions (that may not be accounted in this industry-standard approach) may affect the effectiveness of inhibitor treatment.

Other monitoring techniques include measuring the water composition, utilizing a scale coupon, and measuring weight of suspended solids. In most cases with respect to measuring water composition, the change in water composition by calcium carbonate formation is small and difficult to detect. This may be further complicated by the fact that the composition of water from an aquifer may change with time.

As for scale coupons, the coupons are typically employed with strip coupon holders. Scale coupons are generally rectangular with a series of holes of varying sizes, and utilized to determine scaling tendency. The strength of scaling tendency can be determined by the largest size hole that has accumulated scale. However, to be effective, the coupon should generally be placed where scale is occurring in the water system. Further, use of the scale coupon measures the calcium carbonate attached to the coupon and not suspended particles in the water.

With respect to measuring weight of suspended solids, suspended solids could contain a wide variety of solids in addition to calcium carbonate, such as corrosion products, sand, drilling-mud residual solids, etc. This may also limit the on-line monitoring device based on Thickness Shear Mode Resonator (TSMR), which does not differentiate different types of solids.

As mentioned, EDS (or XRF or XRD if adequate sample solids are available) may be employed to differentiate the different types of solids collected. The solids collected may be suspended solids from the water stream flowing to the injection well. The solids collected may be solid deposits recovered from scraping and pigging operations of water conduits (piping) that convey the water (e.g., aquifer water) to the injection well. These solids (whether suspended solids as collected or solid deposits as collected) may be characterized by EDS analysis to distinguish calcium carbonate solids from other types of inorganic mineral solids, such as dolomite, calcium sulfate, barium sulfate, quartz, clays, iron sulfides, etc. In particular, solids having calcium as the dominant cation as identified via EDS (see, e.g., FIGS. 4, 5, and 22) are characterized as calcium carbonate. Solids not having calcium as the dominant cation as identified via EDS (see, e.g., FIGS. 7-9) are characterized as not being calcium carbonate. The term "dominant" for this technique is defined as being the greatest amount indicated via the EDS spectrum. The dominant cation means the cation as the greatest amount compared to other cations. Like calcium carbonate, minerals or compounds other than calcium carbonate, such as dolomite, calcium sulfate, barium sulfate, quartz, and iron sulfides, may be insoluble in the water, or if dissolved in the water, the physical or chemical conditions of the water can change to initiate precipitation. The water may become supersaturated with respect to one or more of these mineral or compounds, which may thus precipitate.

If sufficient amount of solids are recovered, x-ray diffraction (XRD) or x-ray fluorescence (XRF) can be employed as analytical techniques to determine the composition of solid materials and identify calcium carbonate. XRD or XRF, or both, can be employed in lieu of (or in addition to) EDS to determine which of the solids are calcium carbonate. Yet, again, as appreciated by one of ordinary skill in the art, an adequate amount of collected solids should be available for XRD or XRF analyses.

Whether EDS, XRD, or XRF is utilized to identify solids as calcium carbonate, the calcium carbonate in the recovered solids could originate from sources other than precipitated in the presence of scale inhibitor, and therefore not be a reflection or indication of scale-inhibitor treatment effectiveness. Calcium carbonate solids in the water could originate upstream of the scale-inhibitor injection point. For example, drill cuttings from formation rock of the water supply well that are solids in the water could have calcium carbonate. In another example, solid additives (e.g., bridging agent or weighting material, or both) in the drilling fluid for the drilling of the water supply well can be solids having calcium carbonate that discharge in the water (e.g., aquifer water) produced from the supply well (e.g., water supply well).

With respect to drill cuttings, aquifer reservoirs can be limestone or can be sandstone reservoirs containing calcium carbonate. Thus, residual drilling cuttings (in wellbore) having calcium carbonate could discharge with the aquifer water from the water well and thus are carried by the water supplied for injection. The aquifer water as produced from the water well may include calcium carbonate solids that originated from drilling cuts of rocks (e.g., limestone rocks).

As for additives drilling fluid (or completion or workover fluids), calcium carbonate is utilized (e.g., as a bridging agent) to prevent fluid invasion of permeable zones and to prevent loss of circulation during drilling, workover, and completion activities. Calcium carbonate may be applicable (e.g., as a bridging agent) in aqueous and non-aqueous drilling fluids. The concentrations of the calcium carbonate are typically, for example, 5 parts per billion by weight (ppbw) to 10 ppbw as a bridging agent to prevent fluid loss in workover systems, and 20 ppbw to 40 ppbw, for example, in the preparation of loss control materials (LCM) pills. These calcium-carbonate particle sizes as bridging agent can range, for instance, from 325 mesh (35 μm) to 30 mesh (550 μm). The calcium carbonate in the recovered solids could contain this calcium carbonate introduced upstream of scale inhibitor application locations, which is not related to the inhibitor treatment program.

Embodiments herein distinguish different sources of calcium carbonate in the recovered solids to improve assessment of the scale-inhibitor treatment program. In instances, a $CaCO_3$ solid or particle can be a cluster of single crystals. The suspended solids removed (filtered) from a sample of the water stream, or solid deposits collected from scraping/pigging operations of water piping, are analyzed by SEM (that can be ESEM) to evaluate any identified calcium-carbonate solids for size, shape, and surface morphology utilizing SEM (or ESEM) images at different magnifications. ESEM or SEM imaging analysis (e.g., based on crystal shapes and surface morphologies of the calcium carbonate) may be employed to determine: (1) calcium carbonate scale solids (particles) formed in the presence of scale inhibitor; (2) calcium carbonate solids formed before the inhibitor injection point; (3) calcium carbonate solids that originated from drilling cuts of rocks (e.g., limestone rocks); (4) calcium carbonate solids that were in drilling muds or completion fluids as a bridging agent and/or weighting material. For evaluation via ESEM to identify the calcium-carbonate solids as (1), (2), (3), and (4), see FIGS. 10-21 and associated discussion. The calcium-carbonate solids (1) are the solids of interest in that with effective scale-inhibitor chemical treatment, no calcium carbonate scale particles will typically form after (downstream of) the injection point of the scale inhibitor.

The imaging to determine the origin of the calcium carbonate solids can including imaging techniques other than SEM or ESEM. For example, the imaging may include fluorescence microscopy, transmission electron microscopy (TEM), atomic force microscopy (AFM), and so forth.

FIG. 1 is an injection well 100. Source water 102 may be provided for injection at the injection well 100. The source water 102 may be conveyed via a surface conduit to the injection well 100. The surface conduit may be labeled as piping, pipe, or flowline. The source water 102 may be, for example, produced water, aquifer water, surface water (e.g., seawater, river water, lake water, etc.), or any combinations thereof. Produced water can be water produced along with hydrocarbon from a subterranean formation, and separated from the hydrocarbon. Aquifer water may be from distinct water-bearing formations (an aquifer) and brought to surface with little or no hydrocarbon. The water-bearing formation can be in the same structure (subterranean formation generally) as a hydrocarbon reservoir (e.g., oil reservoir).

Scale inhibitor 104 may be added to the source water 102. The location along the surface conduit (conveying the water) in which the scale inhibitor 104 is added to the source water 102 may be labeled as the addition point 106 (injection point) of scale inhibitor 104. The scale inhibitor 104 is added to the source water 102 to give the water 108 (injection water) that is further conveyed through the surface conduit to the injection well 100 and injected into an oil reservoir via the injection well 100.

The water 108 includes the source water 102 and the scale inhibitor 104. The scale inhibitor 104 may protect piping and equipment downstream of the addition point 106 that are exposed to the water 108 from scale formation. Thus, the scale inhibitor 104 may protect downstream of the addition point 106 the surface conduit (and any associated surface equipment) and downhole components of the injection well 100 from scale formation. The downhole components may include casing, tubulars, and other completion architecture, as well as formation rock.

Scale formation may be the deposition of solids (e.g., $CaCO_3$) (scale solids) that precipitate from the water 108 onto surfaces of the surface conduit (piping), surface equipment, and downhole components. The presence of the scale inhibitor 104 may prevent or reduce scale formation.

Scale is a common term to describe solid deposits that grow over time, blocking and hindering fluid flow through piping, valves, pumps, etc. The scale formation can obstruct flow and damage equipment. Scaling can be a challenge for flow assurance. Examples of scales are calcium carbonate (limescale), iron sulfides, barium sulfate, and strontium sulfate. Scale inhibition may encompass the processes or techniques employed to treat (prevent or reduce) scaling.

At surface, the scale inhibitor 104 may be conveyed in a supply conduit (e.g., small pipe or tubing) to the surface conduit conveying the source water 102, and added to the surface conduit via, for example, a pipe tee. Thus, the addition point 106 may be a pipe tee. Equipment or a pipe fitting other than a pipe tee may be employed to add the scale inhibitor 104 to the source water 102 flowing through the surface conduit.

A scale-inhibitor supply system 110 may provide the scale inhibitor 104 through the scale-inhibitor supply conduit to the addition point 106. The supply system 110 may include a vessel (feed vessel) having scale inhibitor 104. The supply system 100 may include a pump (feed pump) to provide motive force for flow of the scale inhibitor 104 from the vessel through the supply conduit into the addition point 106. The scale-inhibitor feed pump may be, for example, a positive displacement pump (e.g., reciprocating pump). Again, the scale-inhibitor supply system 110 may include a feed vessel and a feed pump.

In operation, the scale inhibitor 104 is pumped via the feed pump from the scale-inhibitor feed vessel through the scale-inhibitor supply conduit into the water 102 flowing though the surface conduit at the addition point 106. The feed pump may be a metering pump in that the feed pump is utilized to control the flow rate (addition rate) (e.g., mass per time or volume per time) of the scale inhibitor 104 through the scale-inhibitor supply conduit and injected at the addition point 106. For instance, the speed or stroke length of the scale-inhibitor feed pump may be altered to adjust the flow rate. The system 110 may include a flow control valve at the feed pump or disposed along the scale-inhibitor supply conduit to control flow rate of the scale inhibitor 104. The scale-inhibitor supply conduit may be, for example, tubing (e.g., capillary tubing).

The flow rate (addition rate, injection rate) of the scale inhibitor 104 via the scale-inhibitor supply system 110 may be specified or adjusted to give a specified concentration, e.g., in parts per million (ppm) by weight or by volume, in the injection water 108 at or above a pre-determined minimum effective dose (MED) of the scale inhibitor 104 in the injection water 108. The flow rate of the source water 102 may be known (e.g., measured via a flow meter) and therefore to give the MED in the water 108, a value of the flow rate of scale inhibitor 104 may be specified. The presence of the scale inhibitor 104 in the water 108 may prevent or reduce scale formation downstream of the addition point 106.

A sample of the water 108 that flows through the surface conduit may be collected from the conduit or other equipment. Because the water 108 has the scale inhibitor 104, the sampling location is downstream of the addition point 106. The suspended solids may be filtered from the collected sample and analyzed.

The internal surfaces of the conduit (piping, flowline) and equipment downstream of the addition point 106 may be scraped to collect solids deposited on the internal surfaces. Solids from the surface conduit may be collected during pigging of the surface conduit. The pigging may be performed via a pig (pipeline pig, utility pig, etc.), which may be labeled as a scraper. The pigging may involve inserting the pig into a pig launcher (also called launching station), which may be an oversized section in the surface conduit. The pig launcher may then be closed and the pressure-driven flow (e.g., of the water) in the conduit pushing the pig along the surface conduit until reaching a receiving trap (pig catcher or receiving station).

The solids collected via scraping or pigging, and the suspended solids removed from the water 108 sample, may be analyzed via EDS, XRD, or XRF to identify solids as calcium carbonate. The solids identified as calcium carbonate may be analyzed via SEM (or ESEM in particular) to determine how much (if any) of the calcium carbonate solids were formed in the presence of the scale inhibitor 104 (which would be downstream of the addition point 106). If determined that calcium carbonate solids are formed in presence of the scale inhibitor, the addition rate of the scale inhibitor may be increased (e.g., via the metering pump) in response.

The injection well 110 includes a wellbore 112 formed through the Earth surface 114 into a subterranean formation 116 (in Earth crust) having an oil reservoir that includes crude oil. Other hydrocarbons may be present in the subterranean formation 116. The injection well 100 may include a surface pump 118 (injection pump) (e.g., centrifugal pump or positive displacement pump) that pumps (injects) the water 108 (e.g., having scale inhibitor 104) through the wellbore 112 into the oil reservoir in the subterranean formation 106. For cased portions of the wellbore 102, the injected water 108 may flow through perforations in the casing into the oil reservoir in the subterranean formation 116. A "surface" pump (or other surface equipment) is a pump (or other equipment) disposed at the Earth surface 114.

In implementations, the injection well 110 may include a vessel 120 that receives the injection water 108 to be pumped (injected) by the surface pump 118. The injection water 108 may flow from the vessel 120 to the inlet (suction) of the surface pump 118. The vessel 120 may be, for example, a tank or container resting on the Earth surface 114 or on a vehicle (e.g., truck) at the surface 114, and the like. The injection well 100 may include a wellhead and other surface equipment.

The water 108 may be injected (pumped) (e.g., via the surface pump 118) into the oil reservoir to maintain pressure (or facilitate pressure maintenance) of the oil reservoir. In implementations, the water 108 may be injected (pumped) into the oil reservoir (e.g., for water flooding) to displace crude oil in the oil reservoir through the subterranean formation 116 toward (and to) a production well. The displaced oil may be produced to Earth surface via the production well (not shown).

The scale inhibitor 104 may be configured to inhibit formation of $CaCO_3$ scale. Scale inhibitor molecules, e.g., either phosphate based or polymer based, may be designed to form an arrangement with, for example, calcium ions ($Ca^{2+}$). In implementations, the scale inhibitor can also adsorb onto calcium salts (carbonate) to prevent or reduce growth of the salts (e.g., threshold effect). The scale inhibitor 104 may be generally soluble in water. The scale inhibitor 104 may be, for example, an organic phosphate(s) or a polyacrylate-based polymeric compound(s). Examples of the organic phosphates include amino tri(methylene phosphonic acid), bis(hexamethylene) triamine penta(methylene phosphonic acid), diethylenetriamine penta(methylene phosphonic acid), 2-phosphonobutane-1,2,4-tricarboxylic acid, and phosphate ester. Examples of the polyacrylate-based polymeric compound(s) include polyacrylate, polymaleic, polyvinyl sulfonate, polyacrylate/polymaleic copolymer, and maleic acid ter-polymer.

Lastly, while the addition point 106 is depicted along the surface conduit conveying the source water 102, the scale inhibitor 104 may instead be added to the upstream source of the source water 102. For some implementations of the source water 102 as aquifer water, the scale inhibitor 104 may be added to the water supply well providing the aquifer water as the source water 102 flowing through the surface conduit.

Figure 2:
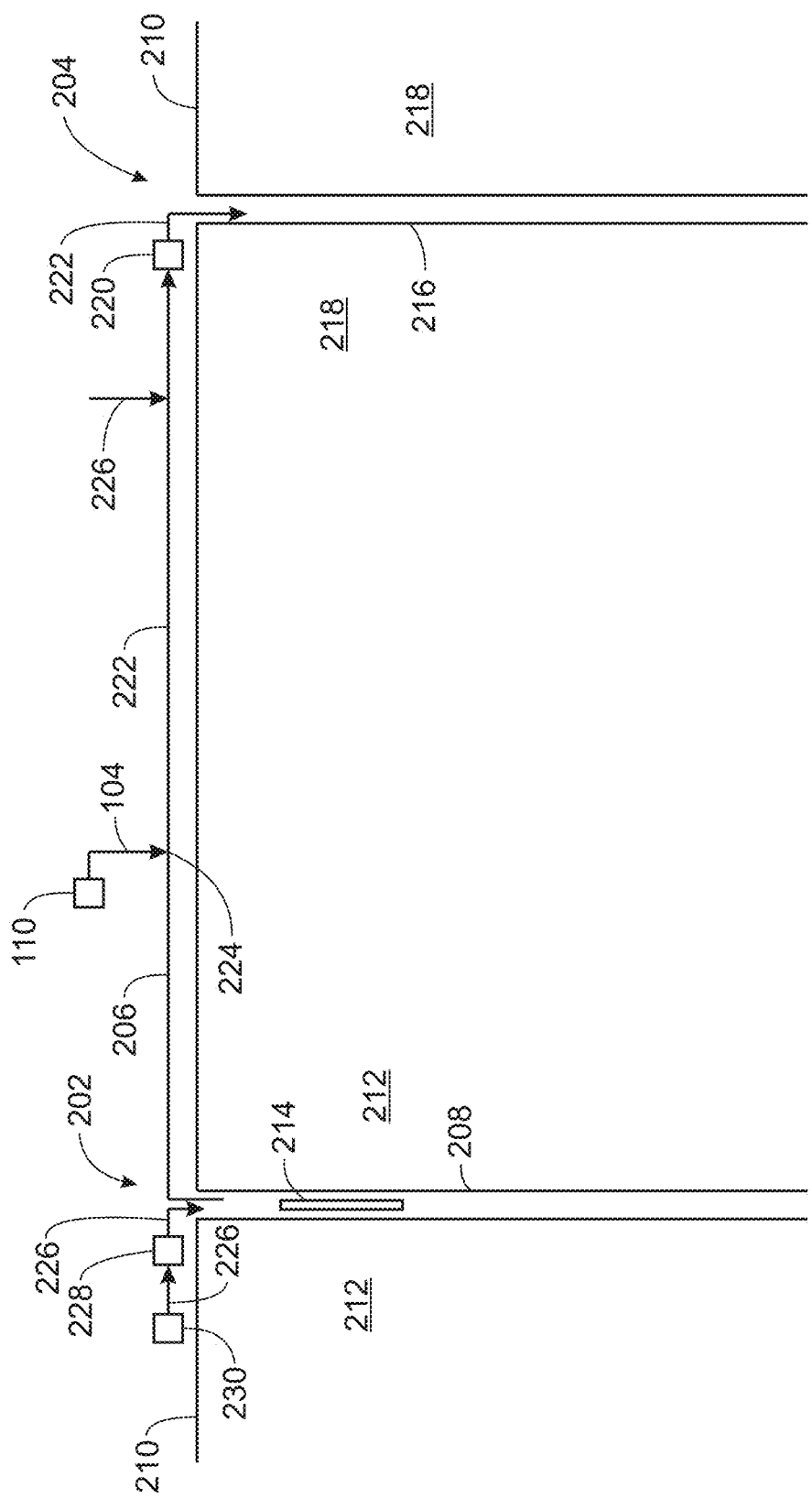
FIG. 2 is a diagram of a water supply well and an injection well.

FIG. 2 is a water supply well 202 (water well) and an injection well 204. The water supply well 202 may supply water to the injection well 204 for injection. In implementations, the injection well 204 may be analogous to the injection well 100 of FIG. 1. The water 206 (source water) supplied from the water well 202 may be analogous to the source water 102 of FIG. 1. Scale inhibitor 104 may be added to the water 206.

The water supply well 202 includes a wellbore 208 formed through the Earth surface 210 into a subterranean formation 212 (in Earth crust) having an aquifer that may be known as an aquifer reservoir or water reservoir. The water supply well 202 may include an electrical submersible pump (ESP) 214 to provide (pump) water 206 from the aquifer to the surface 210. In particular, the water may flow from the aquifer (in the subterranean formation 212) into the wellbore 208 to the pump inlet (suction) of the ESP 214. For cased portions of the wellbore 208, the water may flow from the aquifer through perforations in the casing into the wellbore 208. In operation, the ESP 214 may pump and discharge the received water to the surface 210, such as for provision to the injection well 204 for injection. The water well 202 may include a wellhead and other surface equipment.

The injection well 204 includes a wellbore 216 formed through the Earth surface 210 into a subterranean formation 218 (in Earth crust) having an oil reservoir that includes crude oil. Natural gas and/or other hydrocarbons may be present in the subterranean formation 216. The injection well 204 may include a surface pump 220 (injection pump) (e.g., centrifugal pump or positive displacement pump) that pumps (injects) water 222 through the wellbore 216 into the oil reservoir in the subterranean formation 218. The water 222 injected at the injection well 204 may be water 206 produced (supplied) from the water supply well 202 plus a scale inhibitor 104. The injection water 222 may have a scale inhibitor 104. For cased portions of the wellbore 216, the injected water 222 may flow through perforations in the casing into the oil reservoir in the subterranean formation 218. The water 222 may be injected (pumped) into the oil reservoir to maintain pressure (or facilitate pressure maintenance) of the oil reservoir. The water 222 may be injected (pumped) into the oil reservoir (e.g., for water flooding) to displace crude oil in the oil reservoir through the subterranean formation 218 (e.g., toward a production well).

The water supply well 102 may deliver (produce) water 206, such as via ESP 214, to the surface 210. As discussed, water may flow from the aquifer (in the subterranean formation 212) into the wellbore 208 to the pump inlet of the ESP 214. The ESP 214 may pump and discharge the received water to the surface 210 as the source water 206.

The source water 206 may be conveyed via a surface conduit to the injection well 204. The ESP 214 may provide motive force for the flow. In implementations, a surface pump(s) (e.g., a centrifugal pump as a booster pump) may pump the water 206 (or water 222) to provide additional motive force for flow through the surface conduit (piping).

As discussed with respect to FIG. 1, a scale-inhibitor supply system 110 may provide the scale inhibitor 104 through a scale-inhibitor supply conduit to an addition point 224 (injection point) along the surface conduit. The supply system 110 may include a vessel (feed vessel) having the scale inhibitor 104. The supply system 110 may include a pump (feed pump) to provide motive force for flow of the scale inhibitor 104 (from the feed vessel) through the scale-inhibitor supply conduit into the surface conduit at the addition point 224. As mentioned, the scale-inhibitor feed pump of the supply system 110 can be a metering pump. Therefore, the flow rate (addition rate) of the scale inhibitor 104 may be set and controlled via the scale-inhibitor feed metering pump.

The scale inhibitor 104 is added to the source water 106 (from the aquifer) to give the water 222 for injection at the injection well 204. The presence of the scale inhibitor 104 may inhibit scale formation (e.g., $CaCO_3$ scale) downstream of the addition point 224, such as in the surface conduit (and any associated surface transfer equipment) and on completion structure in the injection well 204.

As indicated with respect to FIG. 1, downstream of the addition point 224, suspended solids from the water 222 and deposited solids from the surface conduit may be collected. These collected solids may be analyzed (e.g., via EDS) to determine if calcium carbonate solids are present. If calcium carbonate solids are not present (e.g., as determined via EDS), the scale-inhibitor treatment (with scale inhibitor 104 at the rate added) may be deemed as effective. If carbonate solids are present (e.g., as determined via EDS), the carbonate solids may be analyzed (e.g., via ESEM imaging) to determine if the carbonate solids were formed upstream of the addition point 224 or downstream of the addition point 224 (in presence of the scale inhibitor 104). If determined that calcium carbonate solids are formed downstream of the addition point 224, the addition rate of the scale inhibitor 104 at the injection point 224 may be increased in response. For example, the pump rate of the scale-inhibitor feed metering pump may be increase.

The injection water 222 having the scale inhibitor 104 may flow through the surface conduit to the injection well 204. In some implementations, supplemental water 226 (e.g., produced water, surface water, etc.) may be added to the injection water for injection.

As mentioned, the surface pump 220 at the injection well 204 may pump (inject) the water In implementations, a vessel (not shown), such as the vessel 120 of FIG. 1, may be disposed upstream of the surface pump 220 to receive the injection water 222 and provide the injection water 222 to the inlet (suction) of the pump 220.

Lastly, the scale inhibitor may be incorporated into the source water upstream of the addition point 224 in lieu of adding scale inhibitor at the addition point 224 to the surface conduit. For example, the scale inhibitor may be batch injected down the backside of the water well 202. In particular, as would be understood by one of ordinary skill in the art, the scale inhibitor may be injected from surface 210 into the wellbore 208 in the annulus between the wellbore casing (wellbore wall) and the production tubing (tubular) (that conveys the water from the wellbore) in the wellbore 208, and such that the scale inhibitor generally does not enter aquifer in the formation 212. The scale inhibitor may enter with water into the ESP 214 inlet. The term backside may mean the backside of the tubular in the casing-tubing annulus.

In another example, the water supply well 202 may be subjected to a batch squeeze treatment in which the scale inhibitor is pumped (injected) from the surface 210 through the wellbore 208 into the aquifer in the subterranean formation 212. In implementations, the scale inhibitor may be retained my reservoir (formation) rock in the aquifer and be gradually released during production of water from the aquifer via the water well 202. In implementations, the treatment life of the batch squeeze treatment (if employed) may be, for example, in the range of 6 months to 12 months, in that the concentration of scale inhibitor in the water may be generally adequate to inhibit scale formation for that time.

Thus, a scale-inhibitor squeeze treatment may be applying pump pressure to force the scale inhibitor into the aquifer. A "batch" squeeze treatment may mean that the scale inhibitor is injected initially as a batch and not on going but intermittently for additional batches. The batch squeeze treatment may include: [1] providing (e.g., pumping) the scale inhibitor through the wellbore 208 of the water supply well 202 into an aquifer in the subterranean formation 212; [2] pumping water (e.g., as an overflush) through the wellbore 208 into the aquifer to displace the scale inhibitor further into the aquifer for interaction with more formation rock; and [3] shutting in the water supply well 202 (e.g., for 4 hours to 24 hours) for interaction of the scale inhibitor with formation rock (reservoir formation rock) in the aquifer (reservoir).

For application (injection) of a scale inhibitor 226 (that may be the same as the aforementioned scale inhibitor 104) as a backside treatment or batch squeeze treatment, a surface pump 228 (e.g., centrifugal pump or positive displacement pump) may pump the scale inhibitor 226 into the wellbore 208. The scale inhibitor 226 (as applied) may thus be present in the source water 206 to give the injection water 222 having the scale inhibitor 226. In implementations, a surface vessel 230 may hold the scale inhibitor 226 for supply to the inlet (suction) of the pump 228. The vessel 230 may be, for example, a tank or container resting on the Earth surface 210 or on a vehicle (e.g., truck) at the surface 210, and the like.

The scale inhibitor 104, 226 as available (e.g., commercially available) may be provided in a formulation (composition) with additional components. These additional components may be included for dilution, as stabilizers (for shelf life), as viscosity modifiers, and so forth. The phrase "scale inhibitor" may refer to the primary or active component(s) (for reducing or preventing scale formation) of the composition received from the vendor. The vendor-supplied formulation having the scale inhibitor 104, 226 may be applied from surface 210, such as via the supply system 110 (e.g., including metering pump) for continuous injection at the addition point 224, and/or provided to the vessel 230 for application in a backside treatment or squeeze treatment of the water supply well 202.

The completion architecture (e.g., wellbore casing and tubing, and associated metal components) and surface structure of the supply well 202 and the injection well 204, as well as the transfer equipment (e.g., surface conduit, etc.) along the surface 210 may typically be metal. The metal may be, for example, mild steel, carbon steel, or stainless steel (or other metal alloys). The metal may be susceptible to scale deposition by the water. The scale inhibitor 104, 226 may interact with (or otherwise address) agents in the water to prevent or reduce (e.g., reduce rate of) scale formation on the metal or other material surfaces.

As indicated with respect to FIG. 1 and discussed with respect to the addition point 224, suspended solids from the water 222 and deposited solids from the surface conduit may be collected. These solids may also be collected in scenarios in which the scale inhibitor is applied to the water well 202 via a backside treatment or batch squeeze treatment. These collected solids may be analyzed (e.g., via EDS) to determine if calcium carbonate solids are present. If calcium carbonate solids are not present (e.g., as determined via EDS), the scale-inhibitor treatment (may be deemed as effective. If carbonate solids are present (e.g., as determined via EDS), the carbonate solids may be analyzed (e.g., via ESEM imaging) to determine if the carbonate solids were formed in presence of the scale inhibitor. If determined that calcium carbonate solids are formed in the presence of scale inhibitor, the addition rate of the scale inhibitor in a backside treatment may be increased, or another batch squeeze treatment may be implemented.

Figure 3:
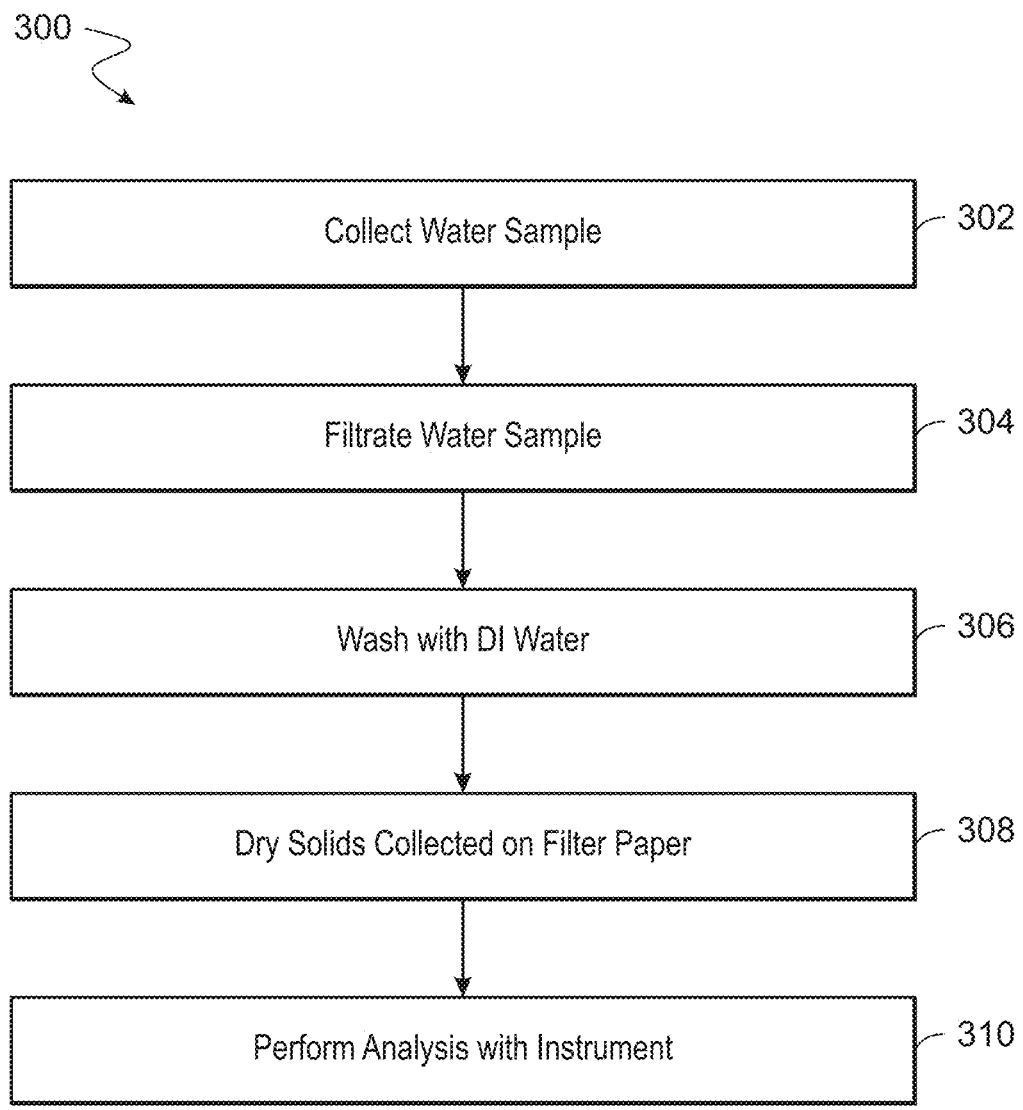
FIG. 3 is a block flow diagram of an example method of collecting suspended solids for analysis.

FIG. 3 is an example method 300 of collecting suspended solids for analysis. At block 302, a sample of water (e.g., 108 of FIG. 1, 222 of FIG. 2) having suspended solids and scale inhibitor is collected. The sample may be collected, for example, from a surface conduit conveying a water stream to an injection well for injection. The volume of the sample collected may be, for example, in the range of 50 milliliters (mL) to 500 mL, or in the range of 100 ml to 250 mL. In implementations, at least 50 mL water should be used due to relatively low suspended solid content in most cases.

At block 304, the method includes to filtrate (filter) the water sample via filtration. This means to filter the water sample accumulating the suspended solids (e.g., on filter paper) while removing the water as filtrate. In particular, a syringe filter with filter paper may be utilized. The pore size (or micron rating) of the filter paper may be, for example, in the range of 0.2 micron (μm) to 0.45 μm. The micron rating is the size at which particles are retained by the filter paper. A syringe filter is a single-use filter cartridge and is generally attached to the end of a syringe for use. A syringe filter may generally consist of a plastic housing with a filter element (e.g., filter paper or membrane). Filtration types or techniques other than a syringe filter can be employed. If on-site filtration is not available, the water sample with suspended solids should generally be brought to laboratory relatively soon after collection. Block 304 may be performed on-site (e.g., via the syringe filter) at or near where the water sample is collected, or can be performed offsite (e.g., via the syringe filter).

At block 306, after filtration, the solids accumulated (collected) on the filter paper are washed with water, such as deionized (DI) water. The volume of DI water for the wash may be relatively small, such as in the range of 10 mL to 15 mL. This washing of the solids may remove residual dissolved salts from the solids.

At block 308, after washing the solid on the filter paper with DI water, the solids on the filter paper are allowed to dry, such as at ambient temperature or in a heated oven (e.g., <100° C.). The solids as dried may then be in condition for analysis via the instruments discussed in block 310. Additional solids that are not suspended solids but are solids collect by scraping or pigging, as discussed, may be subjected to analysis, such as in block 310.

At block 310, the method may include subjecting the dried solids (from block 308) (and any solids from scraping/pigging operation) to analysis via instrument(s). For instance, the solids may be analyzed with an EDS instrument to identify carbonate solids. For any carbonate solids so identified, the carbonate solids may be subjecting to SEM or ESEM imaging to determine if any of the carbonate solids were formed in presence of scale inhibitor utilized in the scale-inhibitor treatment program. In implementations, the EDS instrument or system may be equipped with an SEM system or ESEM system.

The EDS technique employed may detect x-rays emitted from the solid sample during bombardment of the solid sample by an electron beam to characterize the elemental composition. The high-energy electron beam may be like the one SEM. The EDS analysis may be regarded as a non-destructive technique because the specimen (solid sample) prior to analysis does not differ from the specimen after the analysis.

FIGS. 4-9 are typical EDS spectra of common solids in injection waters, such as waters from an aquifer. Calcium carbonate solids may contain up to 10 mol % magnesium, as well as iron or other metal ions, but calcium is the dominant cation. Dolomite contains generally equal amounts of calcium and magnesium.

Figure 4:
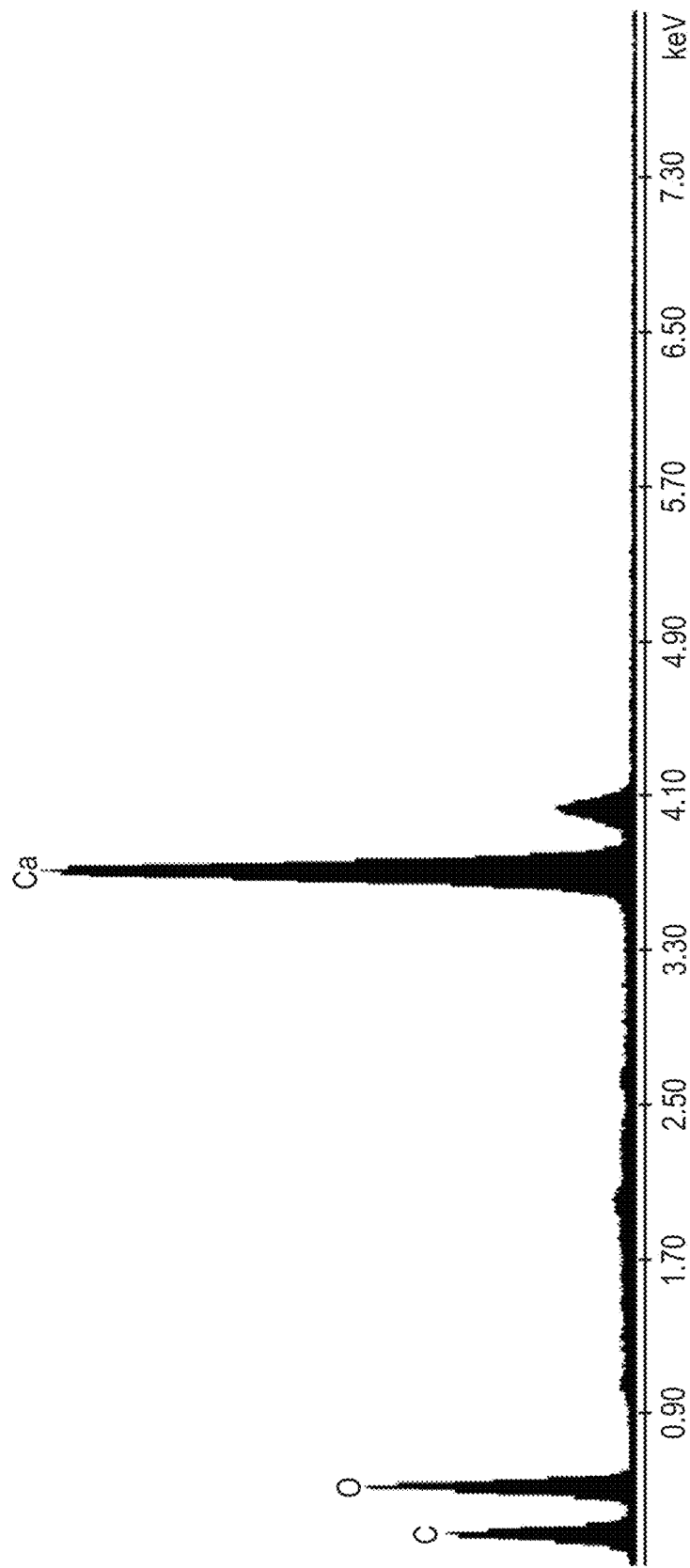
FIGS. 4-9 and 22 are EDS spectra of solids that may be in injection water.

FIG. 4 is an EDS spectrum of calcium carbonate solid particles.

Figure 5:
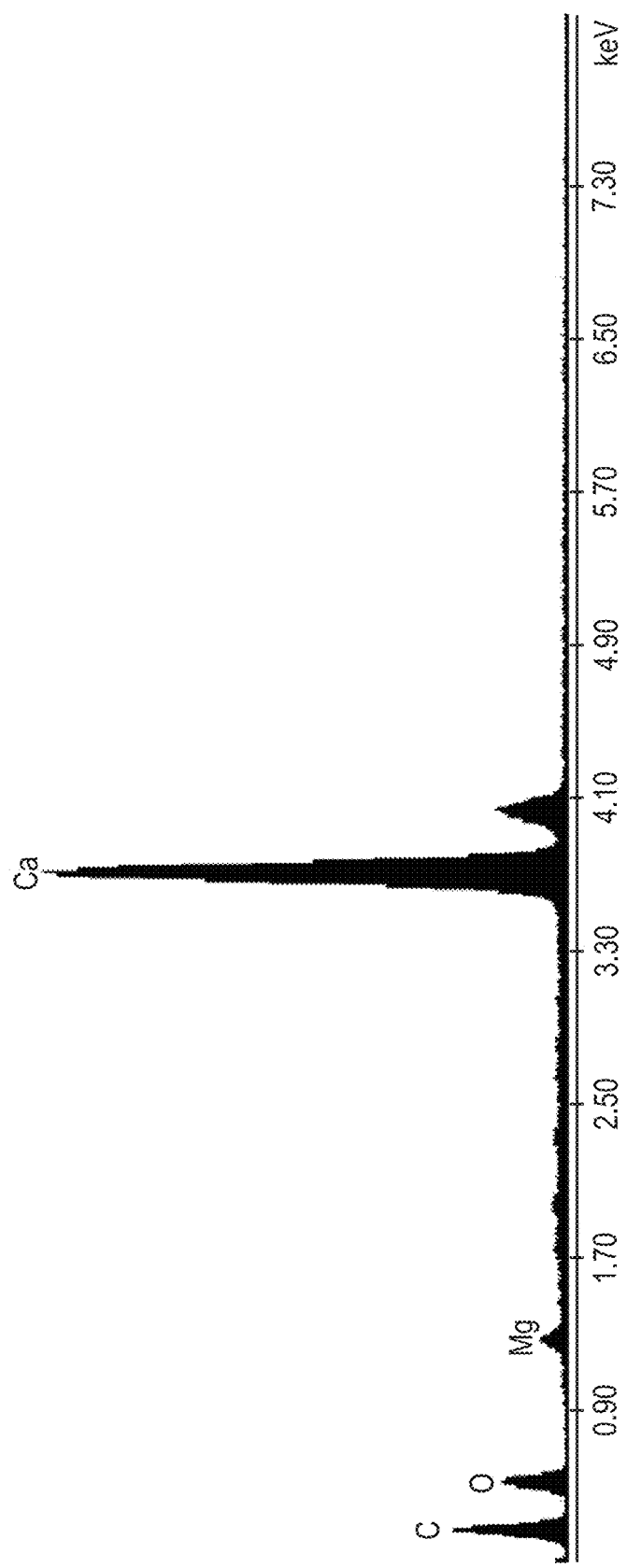

FIG. 5 is an EDS spectrum of calcium carbonate solid particles containing magnesium. As can be seen, calcium is very much the dominant cation.

Figure 6:
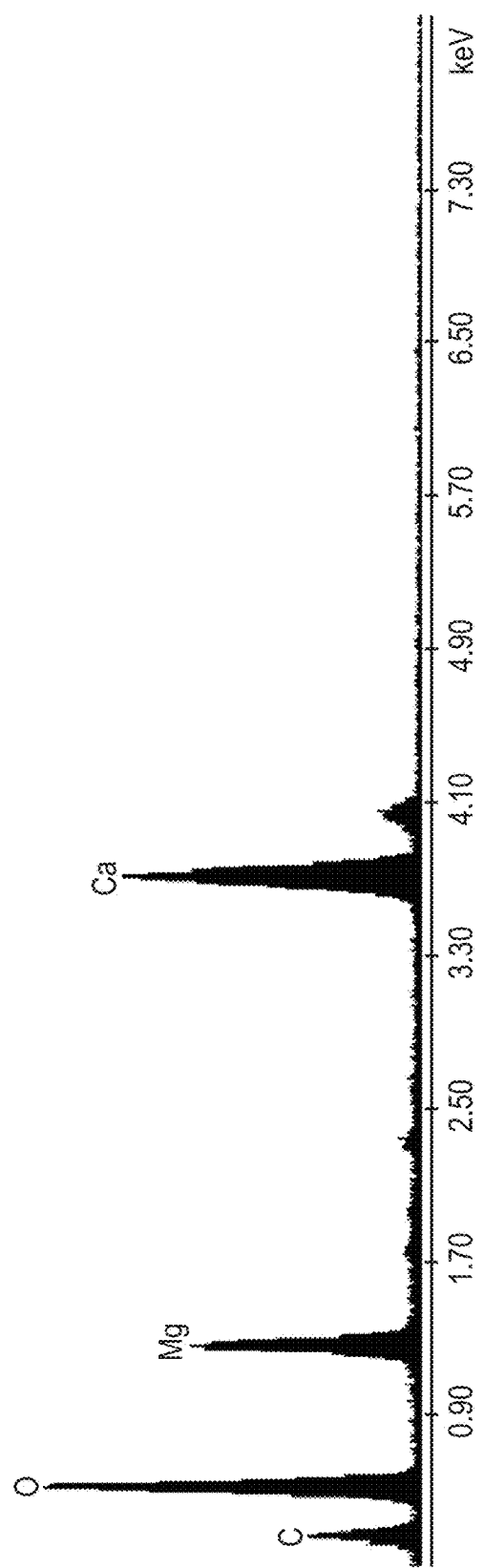

FIG. 6 is an EDS spectrum of dolomite solid particles. Dolomite is an anhydrous carbonate mineral composed of calcium magnesium carbonate $[CaMg(CO_3)_2]$. In the depicted spectrum, calcium is the dominant cation but only slightly. As mentioned, dolomite may generally include substantially equal amounts of calcium and magnesium.

Figure 7:
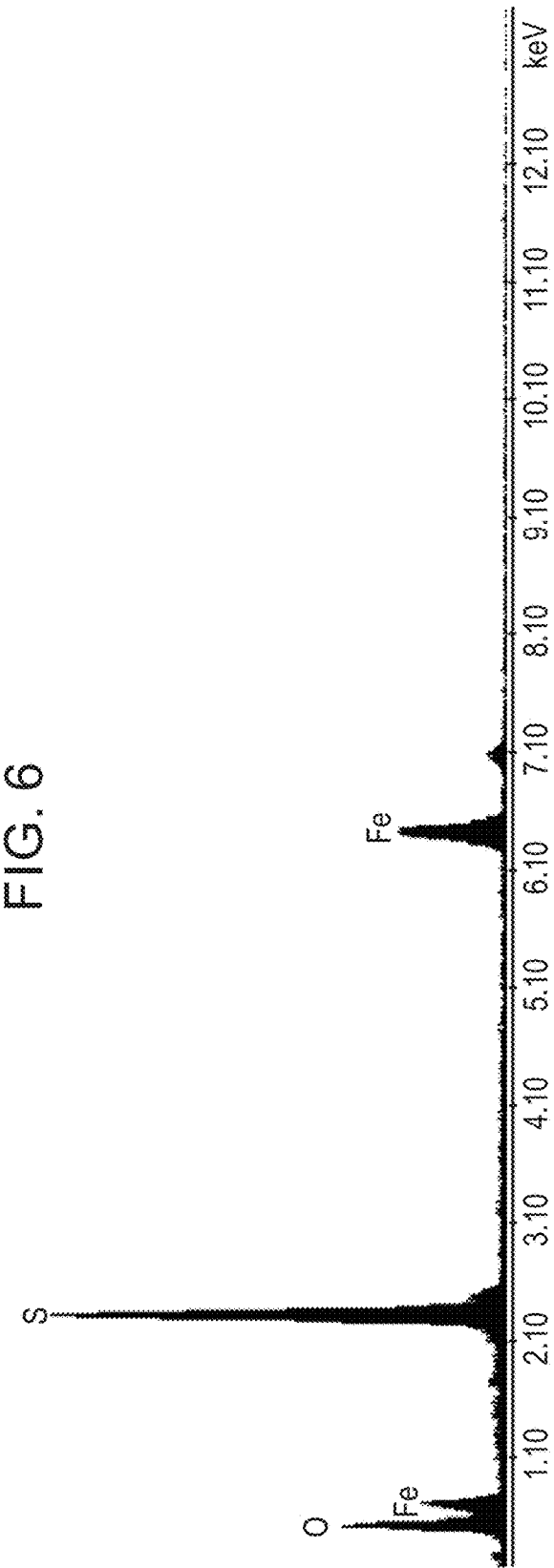
Figure 8:
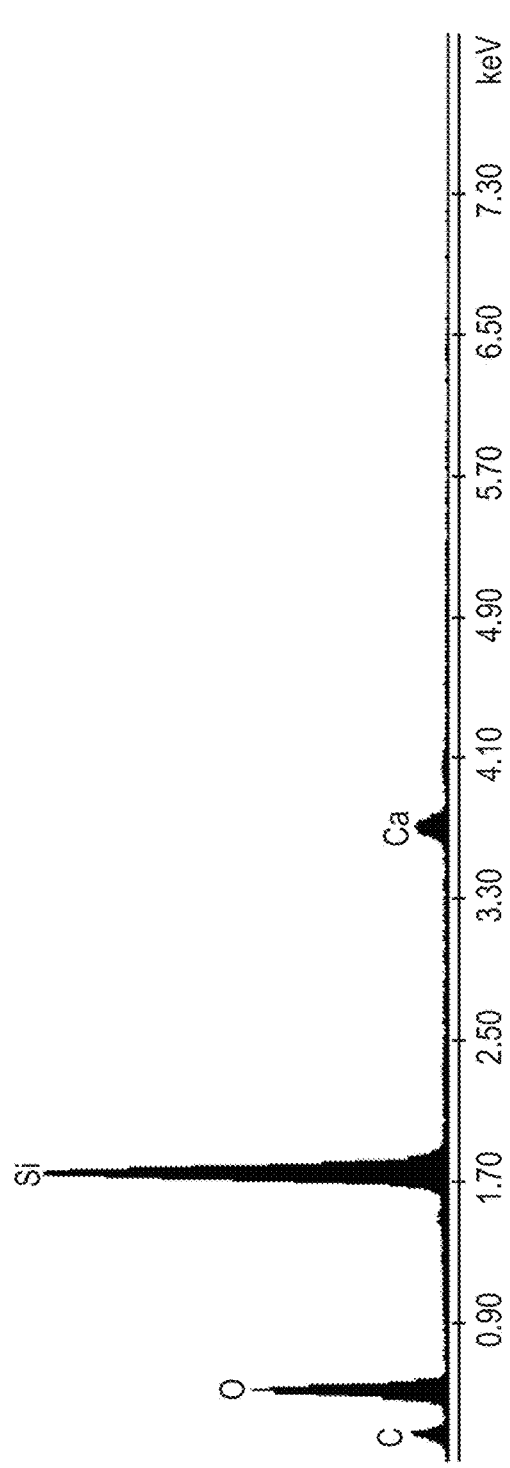

FIG. 7 is an EDS spectrum of solid particles including iron sulfide and iron oxide. FIG. 8 is an EDS spectrum of quartz particles.

Figure 9:
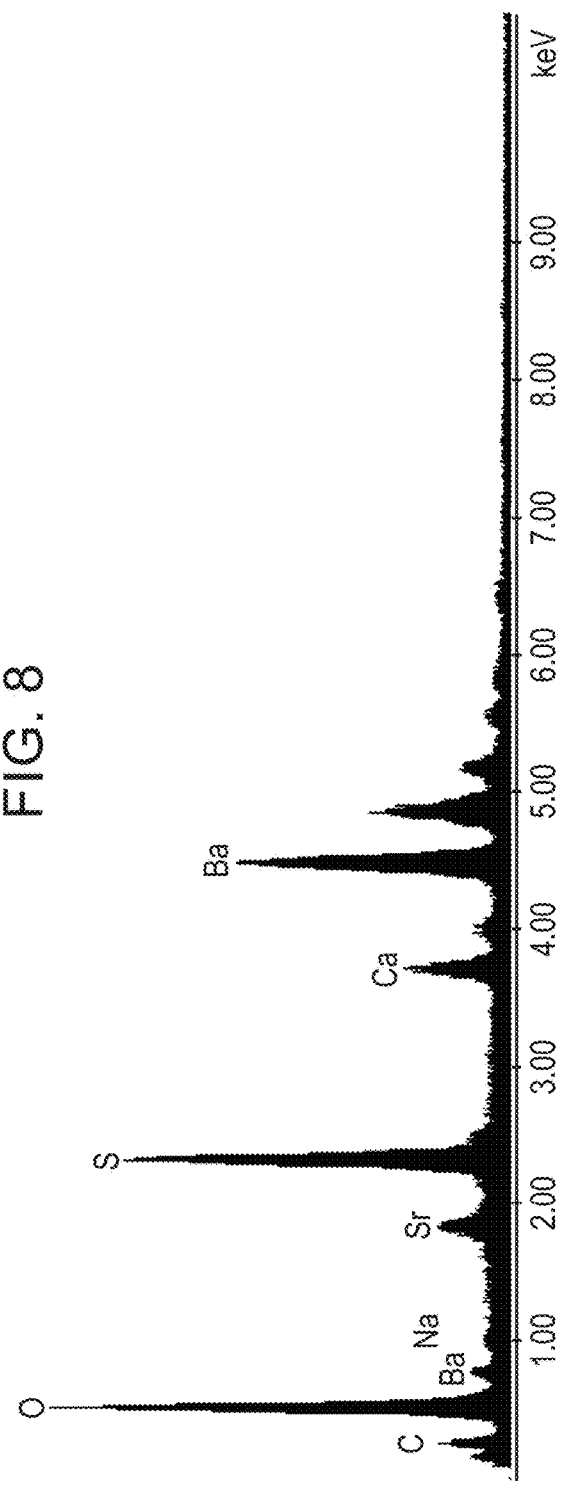

FIG. 9 is an EDS spectrum of solids particles containing primarily barium sulfate. With respect to the calcium peak of significance, such is expected because barium sulfate is generally not pure. In high calcium water, calcium co-precipitates into the barium sulfate lattice.

Again, FIGS. 4-9 are EDS spectra of solids that may be in injection waters (e.g., 108 of FIG. 1 and 222 of FIG. 2). For particles having an EDS spectra showing calcium as the dominant cation, the particle may be deemed identified as a calcium carbonate particle. An exception can be that a particle is deemed identified as not calcium carbonate (instead as dolomite) in which the EDS spectrum shows calcium as the dominant cation but with magnesium cation at an amount within a threshold (e.g., within 20%) of the amount of the calcium cation. In any case, as would be readily appreciated by one of ordinary skill in the art with benefit of the present disclosure, criteria can be developed for deeming particles as identified as calcium carbonate particles and not calcium carbonate particles. Calcium carbonate particles may be particles having at least 80 weight percent (wt %) or 90 wt % of calcium carbonate.

As discussed, particles identified (including deemed identified) as calcium carbonate particles may be subjected to analysis by SEM (which may be ESEM) to determine their origin. In particular, SEM or ESEM imaging may be employed to evaluate size, shape (e.g., geometry generally, crystal shapes, etc.), and morphology (e.g., surface morphology) of the calcium carbonate particles to determine the source of the calcium carbonate particle. In implementations, the identified calcium carbonate solids are not segregated (separated) from the other solids in the sample before the calcium carbonate solids are subjected to imaging (e.g., SEM or ESEM).

Figure 10:
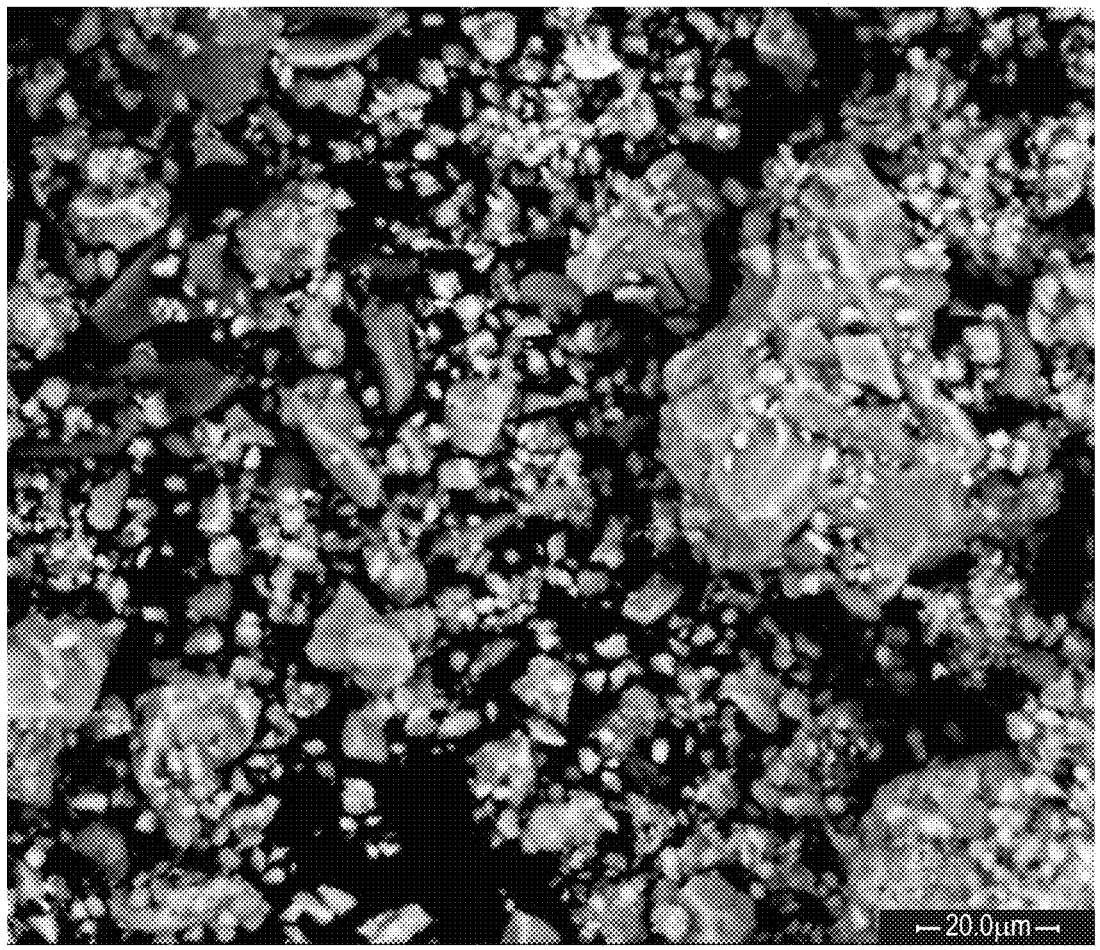
FIGS. 10-21 are ESEM images of calcium carbonate solids.
Figure 11:
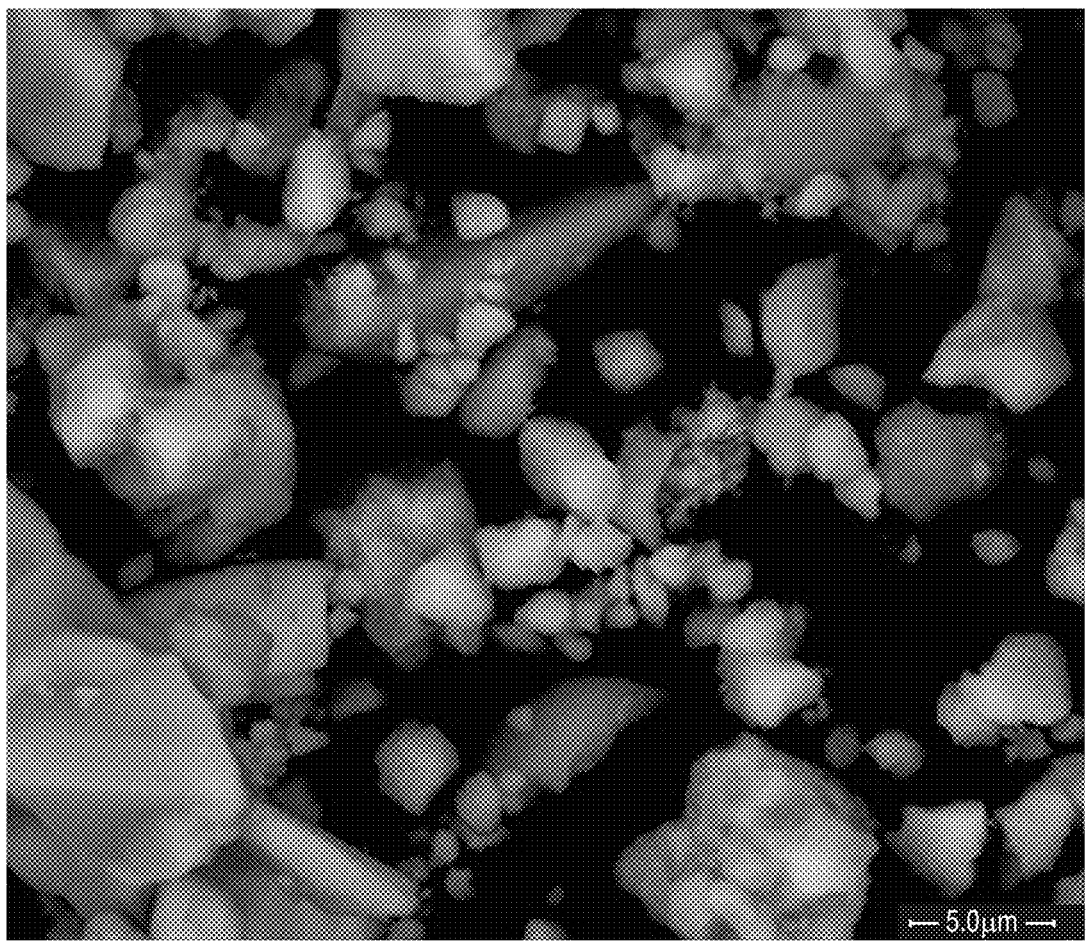

FIG. 10 and FIG. 11 are ESEM images of calcium carbonate solids used in drilling and completion, and that may be a bridging agent and/or weighting agent (weighting material). The FIG. 10 image is at 2000 times (2000×) magnification. The FIG. 11 image is at 8000× magnification. As indicated in the ESEM images (FIGS. 10-11), these calcium carbonate solids utilized during drilling and completion include irregular large particles (>20 microns) and small particles (<20 microns) that are polyhedrons with rough edges and rough corners. These calcium carbonate solids that may be a bridging agent and/or weighting material may have significant presence of (dominated by) the irregular shaped particles of large size (particle size>20 microns). Again, these calcium carbonate solids may have smaller size particles (<10 microns) that are generally a polyhedron in shape. A polyhedron may be a three-dimensional shape (of the solid) with polygonal faces, edges, and corners (or vertices). In the present context a polyhedron is a solid that is three-dimensional as a volume and that can be described by its vertices (corner points), edges (line segments connecting certain pairs of vertices), and faces (two-dimensional polygons). As mentioned, the presence of calcium carbonate solids employed for drilling and completion in the injection water are not an indication of the of the scale-inhibitor treatment. Collected calcium carbon solids having this visual appearance (e.g., in FIGS. 10-11) of the depicted particular larger and smaller particles can be deemed as not formed in the presence of the scale inhibitor.

Moreover, the technique can include obtaining SEM or ESEM images of calcium carbonate utilized as bridging agents and/or weighting agents in the drilling or completion of the actual supply well of interest (e.g., water well 202 of FIG. 2) to compare to SEM or ESEM images of calcium carbonate solids collected (as suspended or scraped) from the system conveying water from the supply well for injection.

Figure 12:
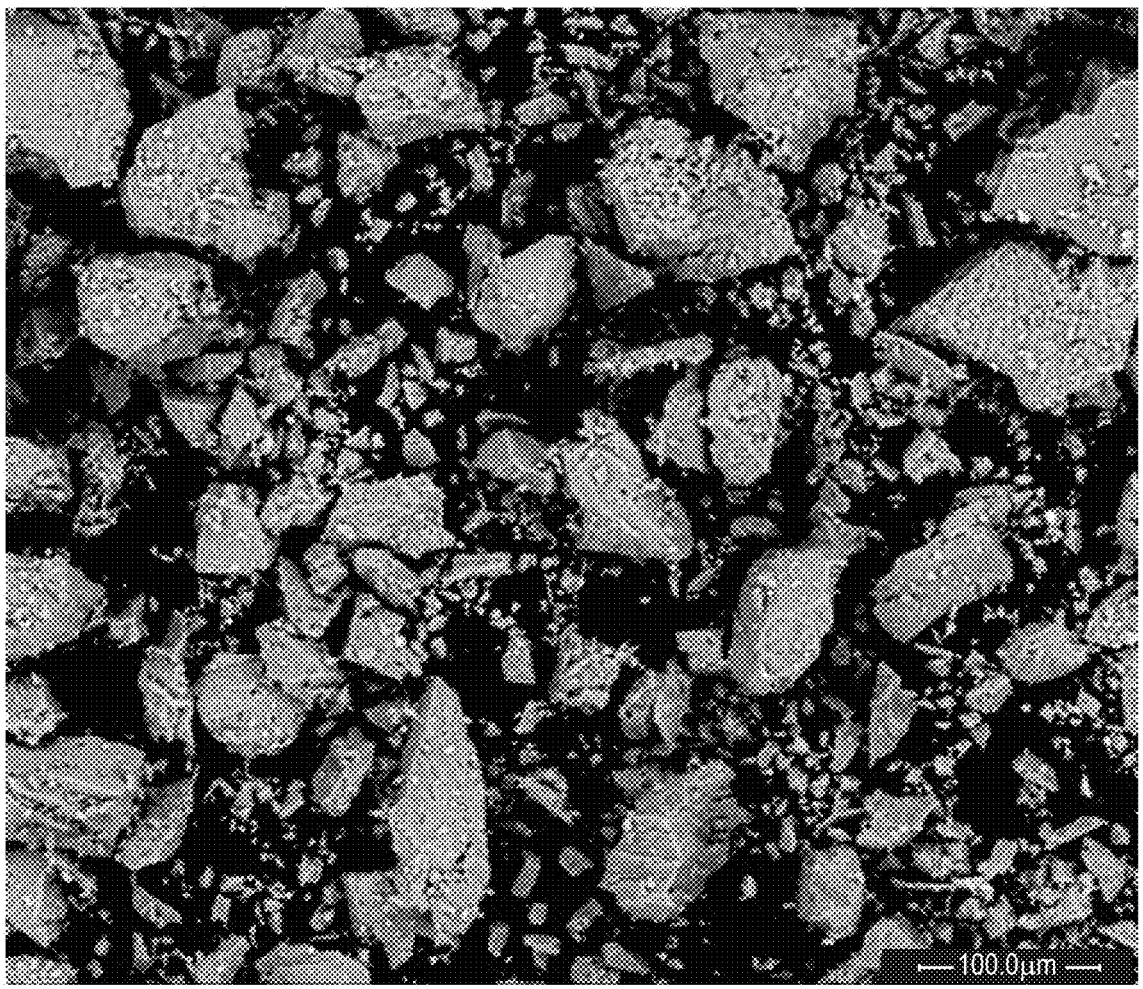
Figure 13:
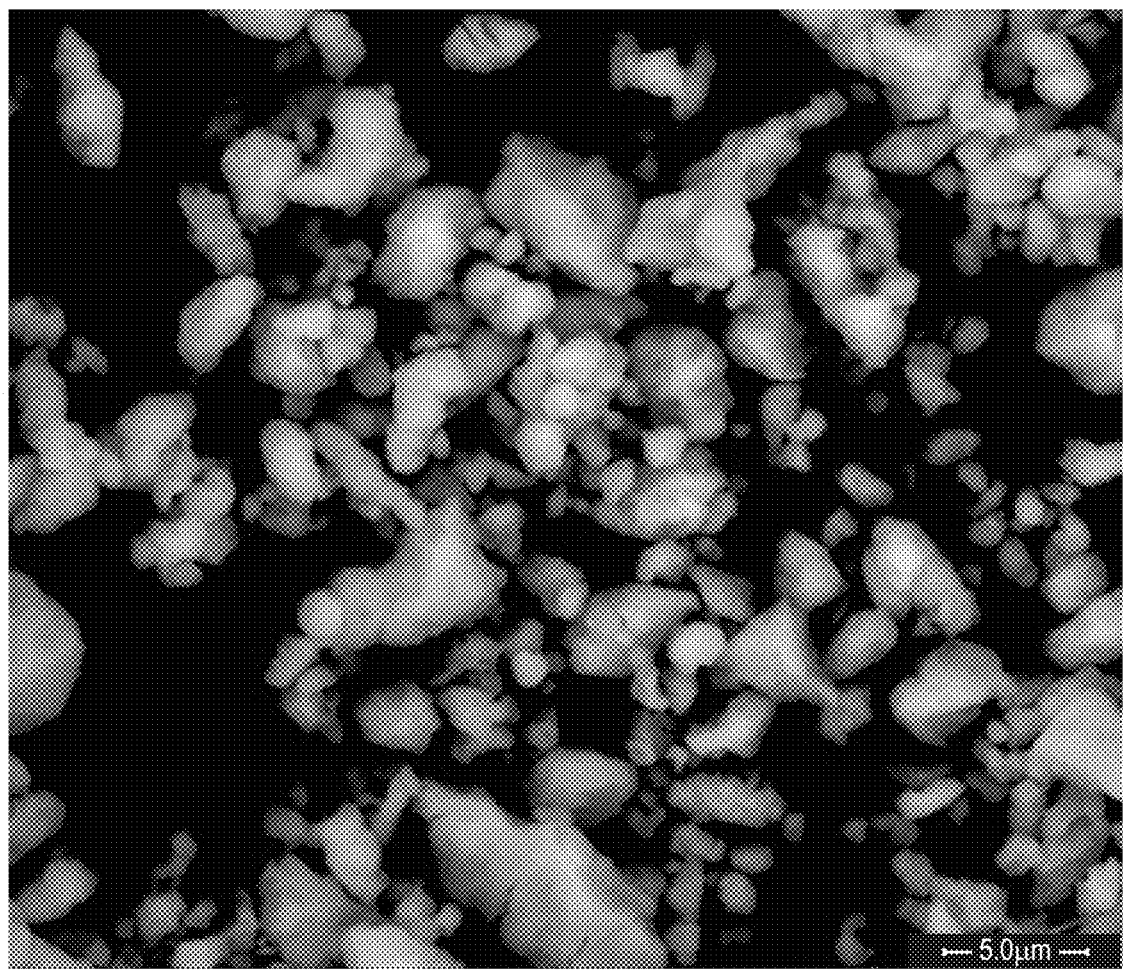

FIG. 12 and FIG. 13 are ESEM images of drilling cuttings of a limestone reservoir (a subterranean formation having limestone rock). The FIG. 12 image is at 500× magnification. The FIG. 13 image is at 8000× magnification. The particles have a similar shape as the calcium carbonate used in drilling and completion. The large sized particles are irregular shaped. At high magnifications, the small size particles can be seen as polyhedrons with blunt edges and corners. These particles (as well as the particles depicted in FIGS. 10-11) are very different shapes from the calcium carbonate particles formed in the injection water and that can lead to scale.

In example tests, calcium carbonate solids (particles) (scale) was prepared (formed) from the synthetic waters based on aquifer water #A 122° F. (50° C.) and aquifer water #B at 176° F. (80° C.). These two aquifer water compositions are listed in Table 1.

TABLE 1

| Aquifer water compositions (gram/liter) | | |
|---|---|---|
| Salt (gram/liter) | #A aquifer water | #B aquifer water |
| NaCl | 7.45 | 76.94 |
| CaCl$_2$ | 7.56 | 15.11 |
| MgCl$_2$ | 1.71 | 2.97 |
| NaHCO$_3$ | 0.69 | 0.36 |
| Na$_2$SO$_4$ | 1.06 | 1.04 |

For these example tests, FIGS. 14-21 show morphologies of calcium carbonate (CaCO$_3$) solids (particles) formed. The ppm given in the list describing FIGS. 14-21 below is ppm by volume. The CaCO$_3$ solids were formed in respective samples of the listed aquifer water. The samples were placed in an oven at the noted temperature for solids to form.

Figure 14:
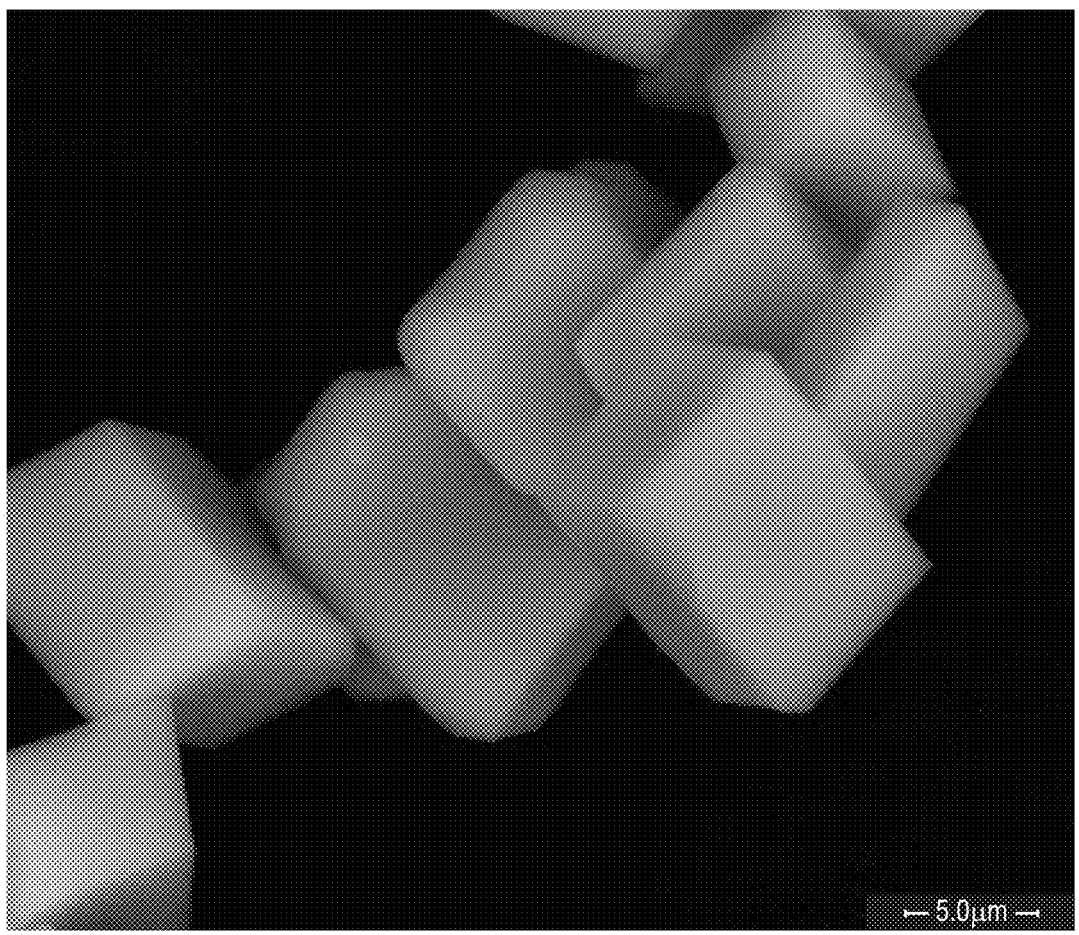

FIG. 14 is CaCO$_3$ solids formed in a sample of aquifer water #A at 50° C. without scale inhibitor.

Figure 15:
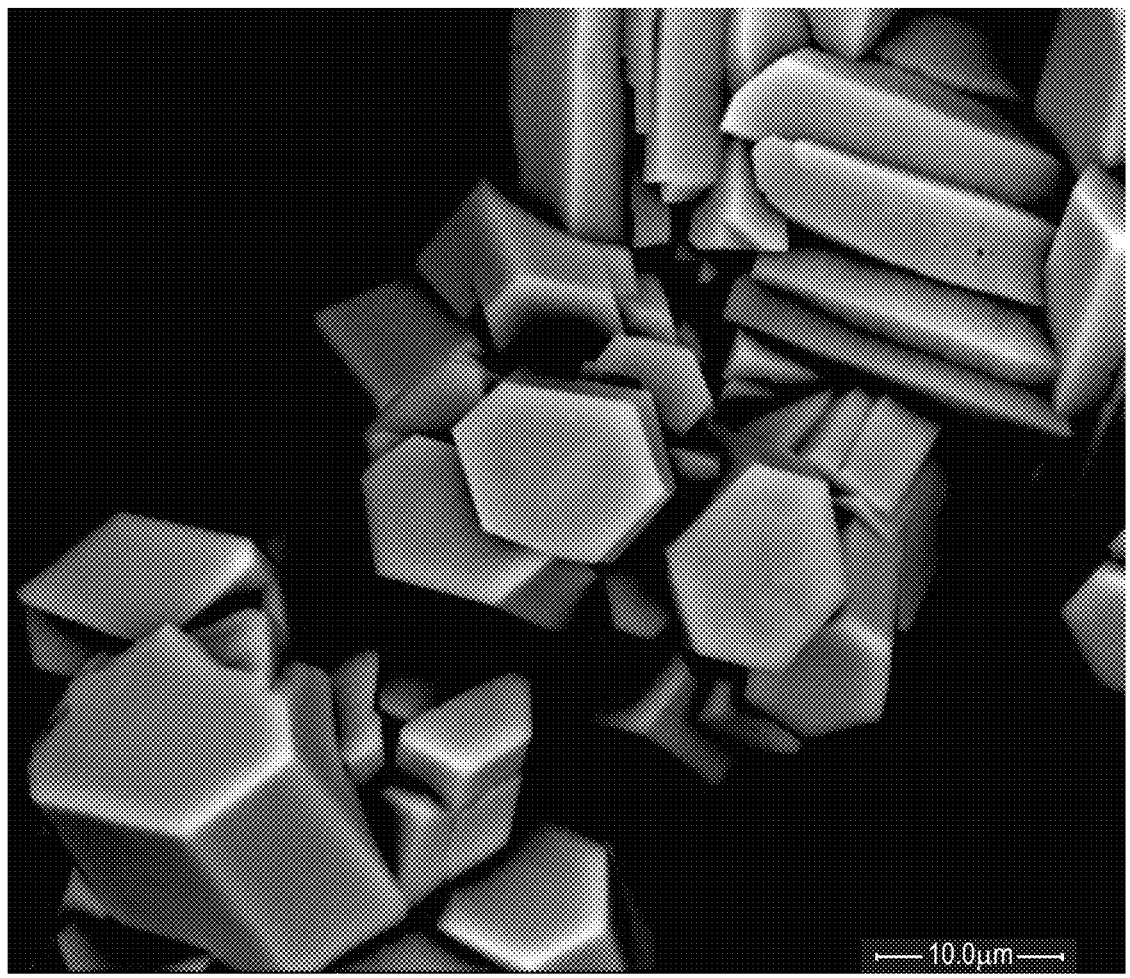

FIG. 15 is CaCO$_3$ solids formed in a sample of aquifer water #B at 80° C. without scale inhibitor.

Figure 16:

FIG. 16 is CaCO$_3$ solids formed in a sample of aquifer water #A at 50° C. with 2 ppmv SI-1 scale inhibitor.

Figure 17:

FIG. 17 is CaCO$_3$ solids formed in a sample of aquifer water #B at 80° C. with 2 ppmv SI-1 scale inhibitor.

Figure 18:
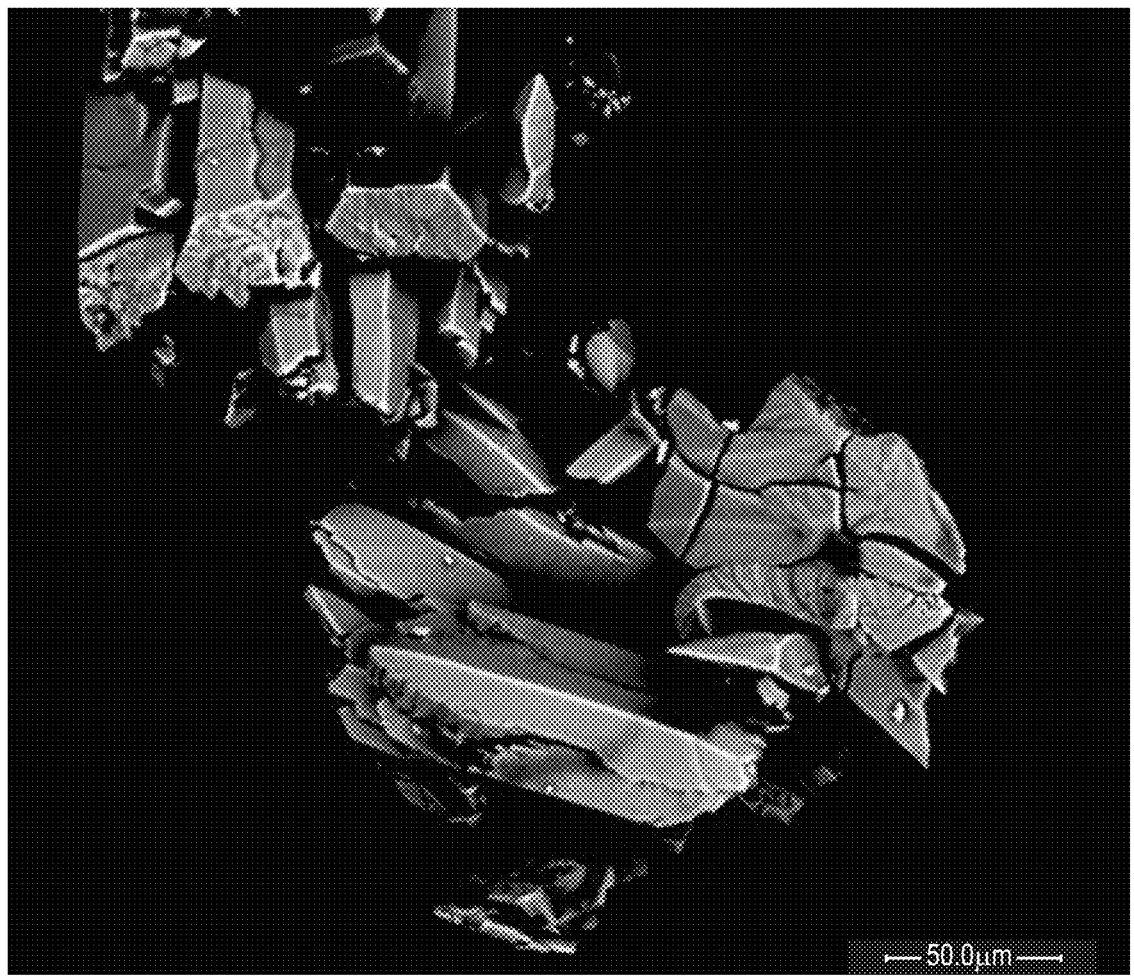

FIG. 18 is CaCO$_3$ solids formed in a sample of aquifer water #B at 80° C. with 10 ppmv SI-1 scale inhibitor.

Figure 19:
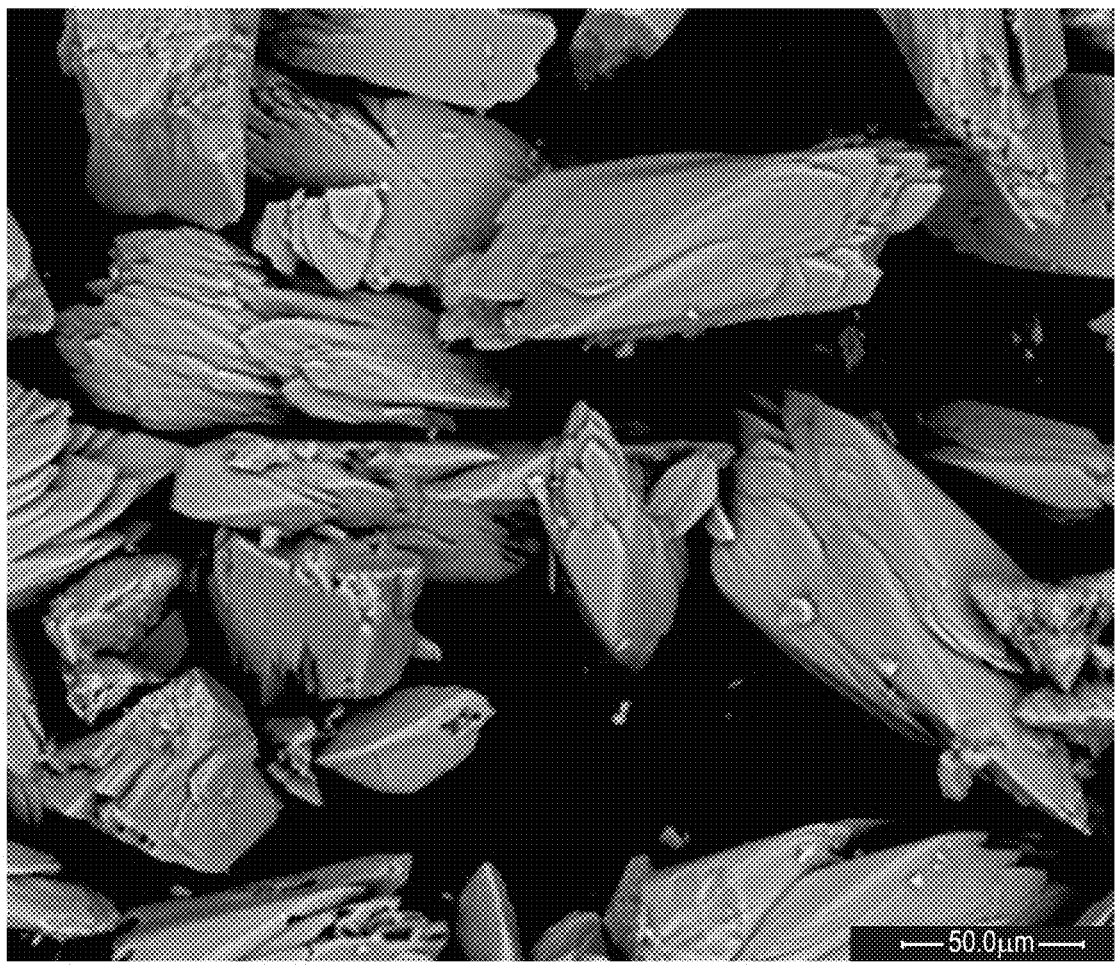

FIG. 19 is CaCO$_3$ solids formed in a sample of aquifer water #B at 80° C. with 5 ppmv SI-2 scale inhibitor.

Figure 20:
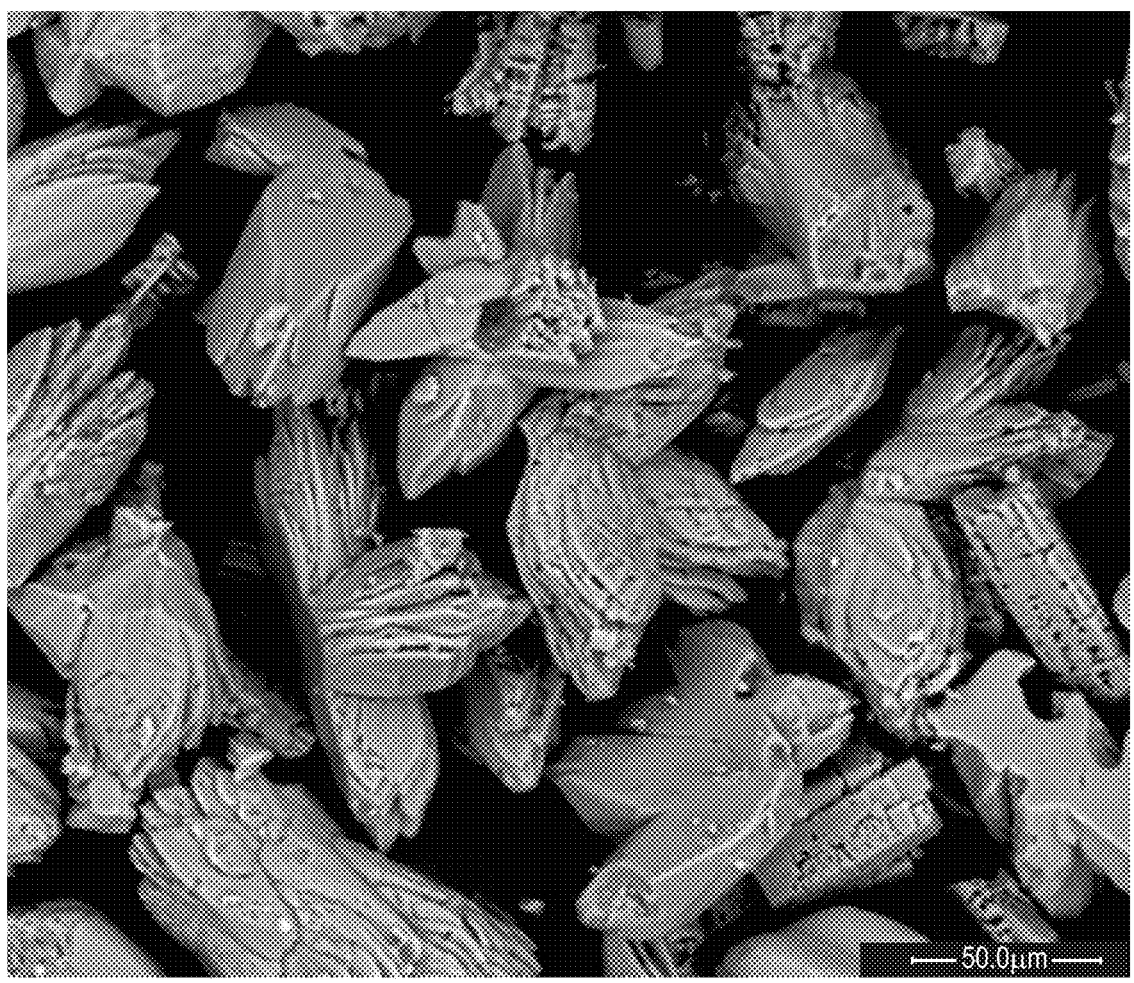

FIG. 20 is CaCO$_3$ solids formed in a sample of aquifer water #B at 80° C. with 10 ppmv SI-3 scale inhibitor.

Figure 21:
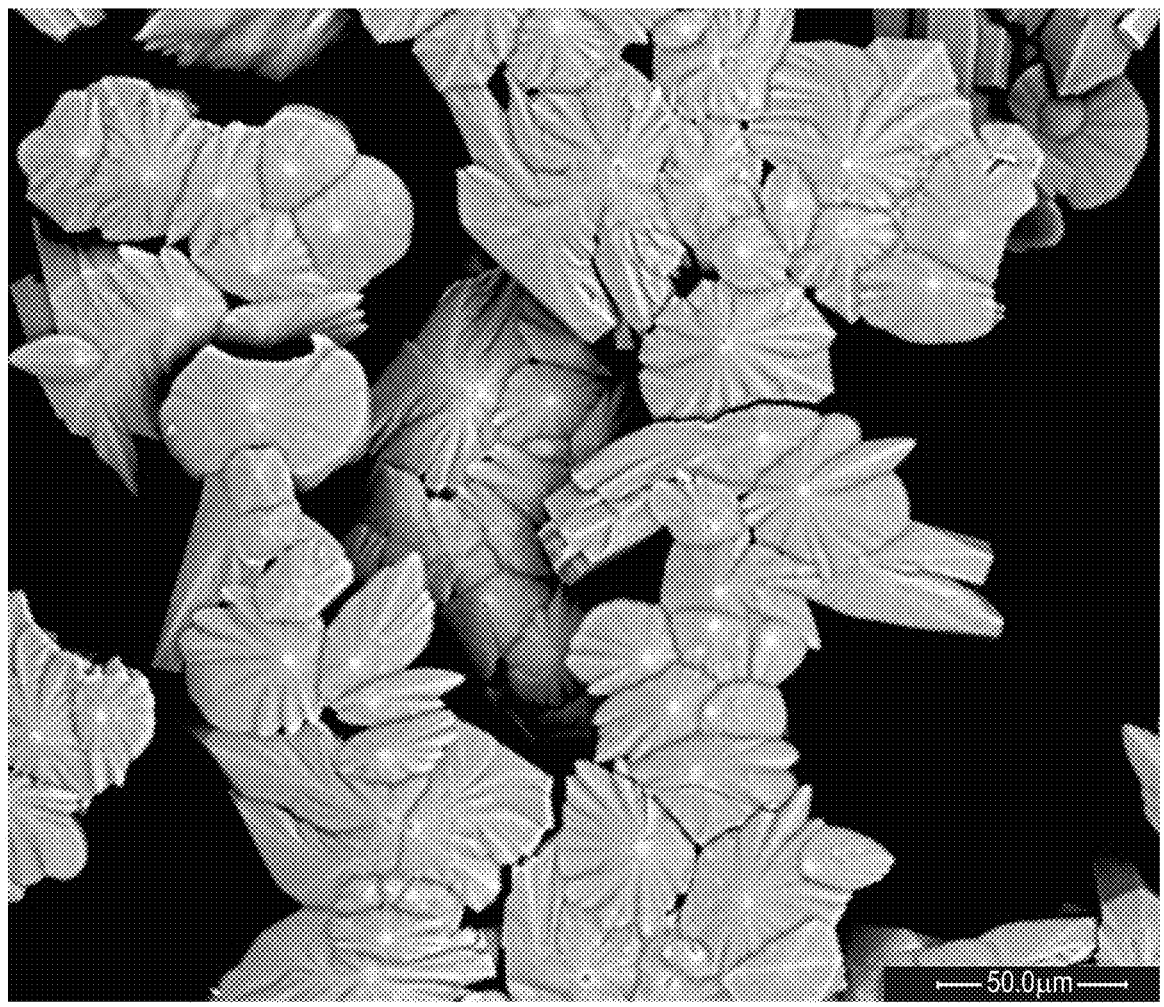

FIG. 21 is CaCO$_3$ solids formed in a sample of aquifer water #A at 50° C. with 5 ppmv SI-2 scale inhibitor.

The term "scale" in application for monitoring and analysis of scale-inhibitor effectiveness may mean both suspended solids in a water sample and solid material deposited on a surface as scale formation.

FIG. 14 is an ESEM image of calcium carbonate solids formed in aquifer water #A at 50° C. without scale inhibitor. FIG. 15 is an ESEM image of calcium carbonate solids formed in aquifer water #B at 80° C. without scale inhibitor. These calcium carbonate particles (formed in absence of scale inhibitor) are rhombohedra and hexagonal. The rhombohedra and hexagonal shapes are characteristic features of calcite and aragonite, respectively. The particles have smooth and flat surfaces with straight edges and intact corners, as indicated in the images in FIGS. 14-15. In implementations, calcium carbonate particles having the visual appearance (shapes, surface morphology) depicted in FIGS. 14-15 can be deemed as calcium carbonate formed not in the presence of scale inhibitor.

Moreover, the technique may [1] sample water (via a well) from an aquifer that is to supply water for injection, [2] form calcium carbonate solids in the water sample (with no scale inhibitor) in the laboratory, and [3] obtain SEM or ESEM images of these formed calcium carbonate solids for comparison to compare to SEM or ESEM images of calcium carbon solids collected (as suspended or scraped) from the system conveying water from the well for injection.

With scale inhibitor, morphology of calcium carbonate solids (scale) formed is changed. The example tests were conducted with three scale inhibitors SI-1, SI-2, and SI-3. SI-1 is Gyptron KT-333 scale inhibitor available from Nalco Champion Chemical Company having headquarters in Sugar Land, Texas, USA. Gyptron KT-333 is a polyacrylate based scale inhibitor. SI-2 is FORSA™ SCW22178 scale inhibitor available from Baker Hughes Company having headquarters in Houston, Texas, USA, and is a pentaphosphonate based scale inhibitor. SI-3 is SCALETREAT 852ND available from Clariant International Ltd. having headquarters in The Woodlands, Texas, USA, and is a sulfonated copolymer based scale-inhibitor.

FIGS. 16-21 are ESEM images of calcium carbonate solids formed in aquifer water in presence of scale inhibitor. The higher the concentration of the scale inhibitor in the aquifer water and/or the more effective or efficient the scale inhibitor, the more the morphology is modified as compared to the calcium carbonate solids formed in the aquifer water with no scale inhibitor. Moreover, while SI-1, SI-2, and SI-3 are evaluated herein as examples of scale inhibitors for their effect on the appearance of the carbonate solids formed in the aquifer water in the presence of the scale inhibitor, other scale inhibitors (e.g., the scale inhibitor employed in a scale-inhibitor treatment program) may be so evaluated.

The technique can include: [1] in the laboratory, forming calcium carbonate solids in a sample of source water (e.g., 102 of FIG. 1) (e.g., aquifer water) (e.g., 206 of FIG. 2) in presence of a scale inhibitor (e.g., a scale inhibitor used or to be used in a scale-inhibition treatment program of the source water for injection); [2] obtaining SEM or ESEM images of the calcium carbonate formed in the laboratory in the source water in presence of the scale inhibitor; and [3] comparing to SEM or ESEM images of calcium carbonate solids collected (as suspended or scraped) from the system conveying water for injection. The comparison may include comparison to SEM or ESEM images of calcium carbonate solids formed in the laboratory in a sample of source water with no scale inhibitor.

FIG. 16 is an ESEM image of calcium carbonate solids formed in a sample of aquifer water #A at 50° C. with 2 ppm by volume (ppmv) of SI-1 scale inhibitor. At 2 ppmv SI-1 in aquifer water #A, calcium carbonate particles formed lose their distinctive sharp edges on the rhombohedrons (rhombohedra) as compared to the calcium carbonate particles (see FIG. 14) formed in a sample of aquifer water #A without scale inhibitor.

FIG. 17 is an ESEM image of calcium carbonate solids formed in aquifer water #B at 80° C. with 2 ppmv of SI-1 scale inhibitor. At 2 ppmv SI-1 in aquifer water #B, calcium carbonate particles lose their flat ends of hexagons as compared to the calcium carbonate particles (see FIG. 15) formed in a sample of aquifer water #B without scale inhibitor.

FIG. 18 is an ESEM image of calcium carbonate solids formed in aquifer water #B at 80° C. with 10 ppmv scale-inhibitor SI-1.

FIG. 19 is an ESEM image of calcium carbonate solids formed in aquifer water #B at 80° C. with 5 ppmv scale-inhibitor SI-2. FIG. 20 is an ESEM image of calcium carbonate solids formed in aquifer water #B at 80° C. with 10 ppmv inhibitor SI-3.

FIGS. 19 and 20 show, respectively, the scale crystals formed in the aquifer water #B with 5 ppmv scale-inhibitor SI-2 and 10 ppmv scale-inhibitor SI-3. Scale-inhibitor SI-3 is slightly more effective than scale-inhibitor SI-1 in preventing the formation of calcium carbonate scale in the aquifer waters, while scale-inhibitor SI-2 is significantly more effective. There are more modifications in scale morphologies by 5 ppmv SI-2 than 10 ppmv SI-1 and SI-3. With 10 ppmv SI-2, no calcium carbonate scale was formed, based on visual observation.

FIG. 21 is an ESEM image of calcium carbonate solids formed in aquifer water #A at 50° C. with 5 ppmv scale-inhibitor SI-2. The ESEM in FIG. 21 shows the calcium carbonate particles formed in aquifer water #A with 5 ppmv inhibitor SI-2, which is very different from the calcium carbonate particles (scale) formed without scale inhibitor.

It is believed that the scale-inhibitor molecules adsorb onto the active crystal growth sites on calcium carbonate surface during the crystal growth and disturb or blocked the normal growth of calcium carbonate crystal. With the presence of scale inhibitors, the crystal lattice has been distorted and therefore the crystal morphology has been changed. When inhibitor concentration exceeds the critical MED (minimum effective dose) value, calcium carbonate scale is prevented by suppressing the formation of stable nuclei.

Scale inhibitor molecules could be incorporated into the distorted calcium carbonate. For scale inhibitors based on organic phosphate, such as phosphonates or phosphate esters, EDS can also be utilized to detect the phosphorous (P) in the calcium carbonate solids (scale). The presence of P is another indicator that the calcium carbonate solid has formed in the presence of inhibitor.

Figure 22:
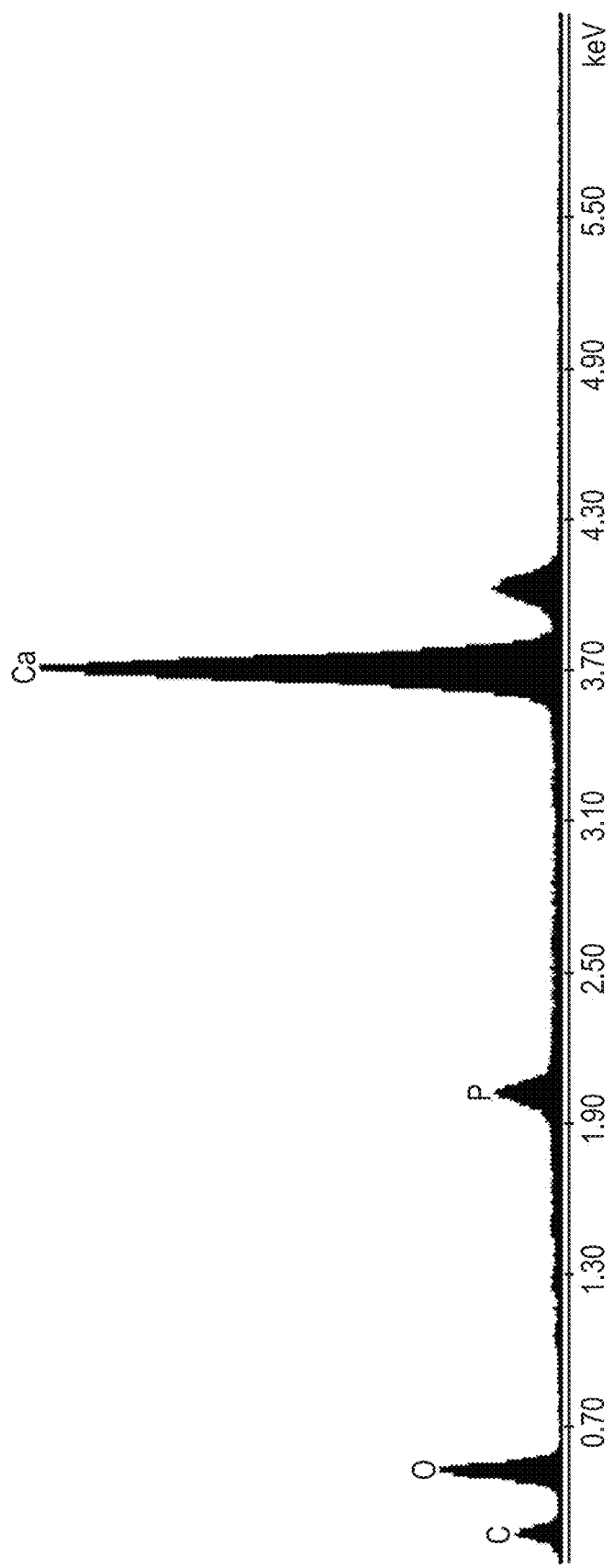

FIG. 22 is an EDS spectrum of calcium carbonate formed in a sample of Jaladi aquifer water with 5 ppmv inhibitor SI-2. There is a clear P signal in the spectrum. The Jaladi aquifer is in Saudi Arabia. Ions in milligrams per liter (mg/L) in the Jaladi aquifer water include sodium (30700 mg/L), calcium (4120 mg/L), magnesium (355 mg/L), bicarbonate (265 mg/L), sulfate (700 mg/L), and chloride (55000 mg/L).

Figure 23:
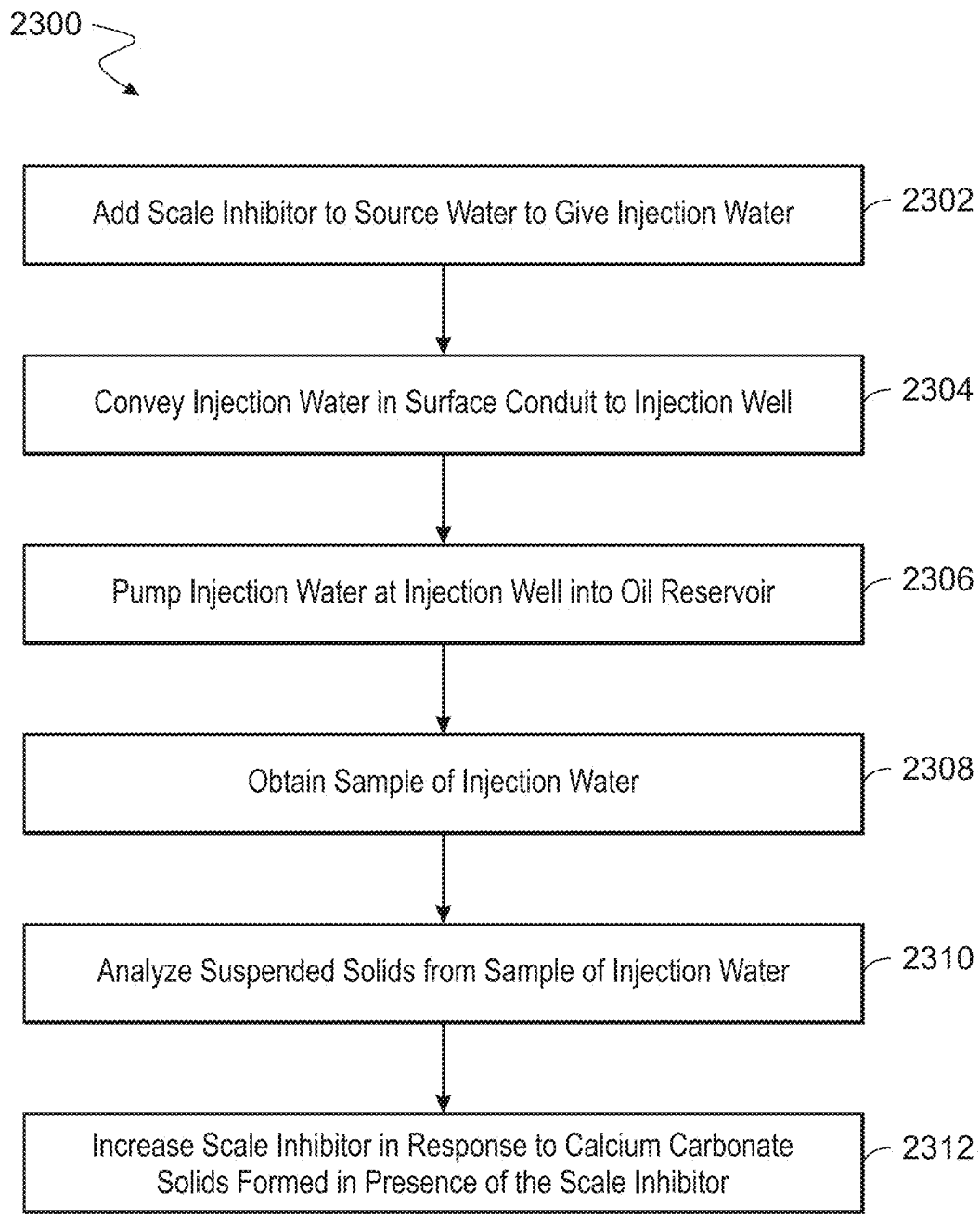
FIG. 23 is a block flow diagram of a method of treatment with scale inhibitor.

FIG. 23 is a method 2300 of treatment with scale inhibitor, such as for a water supply system and associated injection system for injecting supplied water into an oil reservoir. The source water may be aquifer water produced from an aquifer in a subterranean formation via a water well. The source water can be produce water that produce along with hydrocarbon from an oil and/or gas well. The source water can be surface water, such as seawater, river water, lake water, etc. In implementations, the method may include providing, via a water supply well, aquifer water from an aquifer in a subterranean formation as the source water.

The scale inhibitor can be organic phosphate based (e.g., phosphonates or phosphate esters) or polyacrylate based. The scale inhibitor may be (1) an organic phosphate compound, such as a phosphonate or a phosphate ester, or phosphonated carboxylic acids, or (2) a polymeric compound (molecular mass<5000 g/mol) having a carboxyl group, or a polyacrylate. Scale inhibitor molecules, e.g., either phosphate or polymer based, may be configured to form an arrangement with calcium ions ($Ca^{2+}$) and barium ions ($Ba^{2+}$) to inhibit scale formation.

At block 2302, the method includes adding scale inhibitor to source water to give injection water. Again, the scale inhibitor can include, for example, phosphates (e.g., organic phosphate such as phosphonate or phosphate ester) or polyacrylate polymers. In implementations, the adding of the scale inhibitor to the source water may involve adding the scale inhibitor to the source water in a surface conduit that is routing (conveying, transporting) the source water to the injection well. A "surface" conduit is a conduit at Earth surface (e.g., 114 of FIG. 1, 210 of FIG. 2). The scale inhibitor may be added (injected) at an addition point (injection point) along the surface conduit. In those implementations, the surface conduit upstream of the addition point may convey the source water, and downstream of the addition point convey the source water as injection water having the scale inhibitor. As discussed with respect to the scale-inhibitor supply system 110 of FIGS. 1-2, the scale inhibitor may be injected at the addition point via a metering pump. The method may include adding scale inhibitor to source water to give injection water for injection via an injection well into an oil reservoir including crude oil. The source water flowing through the surface conduit can be aquifer water (e.g., from a water supply well), produced water (e.g., that was produced along with hydrocarbon), or surface water (e.g., seawater), or any combinations thereof. The method may include providing, via a water supply well, aquifer water from an aquifer in a subterranean formation as the source water into the surface conduit, and wherein adding the scale inhibitor to the source water includes adding the scale inhibitor to the surface conduit to give the injection water conveyed in the surface conduit.

For the source water as aquifer water produced from a water supply well into the surface conduit, the adding of the scale inhibitor to the source water may include adding the scale inhibitor to the surface conduit to give the injection water conveyed in the surface conduit. As mentioned, the scale inhibitor may be injected into the surface conduit by a scale-inhibitor supply system (e.g., 110 of FIGS. 1-2) including, for example, a positive-displacement metering pump.

For the source water as aquifer water, the adding of the scale inhibitor to the source water may be a backside treatment of the water well (supplying the aquifer water) with the scale inhibitor. The adding of the scale inhibitor to the source water may involve adding the scale inhibitor via a backside treatment with the scale inhibitor to a water supply well that provides the source water. The scale inhibitor may pumped down the backside of the water supply well. In other words, the scale inhibitor may be pumped from surface into the casing-tubing annulus in the wellbore of the water well. The scale inhibitor as discharged from the annulus at a bottom portion of the wellbore may then flow upward into the tubing (e.g., production tubing) with the aquifer water to the surface. In implementations, the scale inhibitor along with the aquifer water may flow into the pump inlet of an ESP to be pump through tubing to the surface.

For the source water as aquifer water, the adding of the scale inhibitor to the source water may be a batch squeeze treatment of the water well (that supplies the aquifer water) with the scale inhibitor. The adding of the scale inhibitor to the source water may involve adding the scale inhibitor via a squeeze treatment with the scale inhibitor of a water supply well that provides the source water. Downhole chemical squeeze treatments for deploying scale inhibitors to protect wellbores and downhole production tubulars from mineral or inorganic deposits may typically have relatively good (long) lifetimes. Variables affecting a scale-inhibitor squeeze treatment may include the amount and concentration of scale inhibitor, volume of aquifer formation to contact, amount of overflush, well shut-in time, etc. The squeeze treatment with the scale inhibitor may be a type of inhibition treatment employed to control or prevent scale deposition. In a scale-inhibitor squeeze, the inhibitor may be pumped into a water-producing zone. The scale inhibitor may attach to the formation matrix (rock), for example, by chemical adsorption or by temperature-activated precipitation, and returns with the produced aquifer water at sufficient concentration to reduce or avoid solids (scale) precipitation.

Batch squeeze treatment of water supply wells may involve pumping scale inhibitor, either neat or diluted, into the well to the aquifer reservoir layer, followed by pumping water into the well to push the scale inhibitor away from the wellbore into the aquifer. The pumping of the scale inhibitor and the follow-up push water may expose the pumped scale inhibitor to reservoir rocks for interaction of the scale inhibitor with the reservoir rock. The pumping of the follow-up water push may be designed (configured) to expose the pumped scale inhibitor to more reservoir rocks for more interaction of the scale inhibitor with the reservoir rock. The well may be shut in (e.g., for a duration in the range of 4 hours to 24 hours) to allow the pumped scale inhibitor to react with reservoir rocks and be retained. When water production from the water source well (from the aquifer reservoir) is initiated or resumes, the retained scale inhibitor may release slowly or gradually into the water stream to provide long-term protection. In contrast, chemicals not retain flow back quickly with the produced water.

Scale inhibitor typically beneficially has strong interaction with the reservoir rocks (e.g., in particular with carbonates and clays), and can be effective at low concentration [e.g., 2 parts per million (ppm) to 5 ppm) by volume] in the produced supply water to prevent or reduce scale formation (e.g., calcium carbonate scale formation) by the supply water. Thus, for scale inhibitors, this may yield long squeeze treatment life, e.g., in the range of 6 months to 12 months.

The water well may pump the aquifer water with scale inhibitor (applied via the batch squeeze treatment or by the aforementioned backside treatment) as injection water to surface. This injection water as the produced aquifer water with scale inhibitor may flow (discharge) through a wellhead at the water well into a surface conduit that conveys the injection water to an injection well. As also discussed, the injection water may be source water (e.g., aquifer water, produced water, and/or surface water) with the scale inhibitor added to a surface conduit conveying the source water to give the injection water.

The injection water (whether the scale inhibitor is introduced via backside treatment, squeeze treatment, or addition to surface conduit) may be conveyed (e.g., through the surface conduit) (block 2304) to the injection well for injection into an oil reservoir by an injection pump at the injection well.

At block 2304, the method includes conveying the injection water in a surface conduit to an injection well to be injected into an oil reservoir in a subterranean formation. One or more pumps may provide motive force for flow of the injection water.

At block 2306, the method includes injecting (pumping) (e.g., via a surface pump) the injection water through a wellbore of the injection well into the oil reservoir in the subterranean formation. The injection well may include the wellbore as formed through Earth surface into the subterranean formation in Earth crust.

At block 2308, the method includes obtaining a sample of the injection water, wherein the sample of the injection water includes suspended solids. In implementations, the sample of injection water may be collected from the injection water flowing through the surface conduit, such as at a sample point.

At block 2310, the method includes analyzing the suspended solids from the sample of the injection water. The analyzing may include analyzing the suspended solids via EDS, XRD, or XRF, or any combinations thereof, to identify calcium carbonate solids (if present) of the suspended solids. The method may include determining via the analyzing that that the suspended solids do not include calcium carbonate solids, and then deeming that the treatment with the scale inhibitor as effective in response to determining that the suspended solids do not comprise calcium carbonate solids. The method may include determining via the analyzing that the suspended solids include calcium carbonate solids, and then imaging (discussed below) the calcium carbonate solids. In implementations of the initial analysis to determine if calcium carbonate solids are present, the suspended solids are analyzed by EDS. EDS can be characterized as microanalysis. The analyzing of the suspended solids (to determine if calcium carbonate solids are present) may involve separating (filtering) the suspended solids from the sample of injection water, drying the suspended solids as separated, and analyzing the suspended solids as separated and dried via EDS, XRD, or XRF, or any combinations thereof. The method can include collecting deposited solids from an internal surface of the surface conduit downstream of the addition point, wherein analyzing the suspended solids is more broadly analyzing solids including the suspended solids and the deposited solids, wherein the analyzing comprises EDS, XRD, or XRF, or any combinations thereof.

The aforementioned imaging of identified calcium carbonate solids (if present and identified) may be SEM. The SEM can be ESEM. The imaging may employed to determine if any of the calcium carbonate solids formed in the presence of the scale inhibitor. The method may include determining via the imaging that the calcium carbonate solids do not include calcium carbonate solids formed in presence of the scale inhibitor, and deeming that the treatment with the scale inhibitor as effective in response to determining that the calcium carbonate solids do not include calcium carbonate solids formed in the presence of the scale inhibitor. The method may include determining via the imaging that the calcium carbonate solids include calcium carbonate solids formed in presence of the scale inhibitor. Therefore, the method may include analyzing the calcium carbonate solids via imaging, thereby identifying at least some of the calcium carbonate solids as formed in presence of the scale inhibitor. Again, the imaging may be, for example, SEM or ESEM, or both At block 2312, the method includes increasing the amount of scale inhibitor added (adding more of the scale inhibitor) to the source water in response to the analyzing (block 2310) determining that the suspended solids include calcium carbonate solids formed in the presence of the scale inhibitor. Thus, for continuous injection of the scale inhibitor, the addition rate of the scale inhibitor may be increased in response to identifying at least some of the calcium carbonate solids as formed in the presence of the scale inhibitor. The amount of the scale inhibitor incorporated into the source water may be increased such that carbonate solids do not form in the presence of the scale inhibitor.

Again, in response to detecting (in block 2310) that calcium carbonate solids formed in the presence of the scale inhibitor are present, the amount of scale inhibitor added to the source water may be increased. For example, in the continuous injection of scale inhibitor at an addition point (injection point) along a surface conduit conveying the source water, the addition rate (injection rate) of the scale inhibitor may be increased. For instance, a metering pump in a scale-inhibitor supply system (e.g., 110 of FIGS. 1-2) may be adjusted to increase the addition rate (amount pumped by the metering pump).

For the example of backside injection of scale inhibitor to a water supply well providing aquifer water as the source water, the amount of the backside injection of the scale inhibitor may be increase. For the example of a batch squeeze treatment of scale inhibitor to a water supply well (providing aquifer water as the source water) that gave the scale inhibitor for the source water, another batch squeeze treatment may be implemented. The treatment life of the previous batch squeeze treatment of scale inhibitor may have expired. A new batch squeeze treatment of scale inhibitor may be applied to increase the concentration of the scale inhibitor in the injection water such the calcium carbonate particles do not form in the presence of the scale inhibitor.

Lastly, solids (scale) (e.g., iron sulfides, barium sulfate, calcium sulfate, strontium sulfate, etc.) other than calcium carbonate may form with the above-discussed source waters for injection. While the discussion herein has focused on calcium carbonate, embodiments of the present techniques may be applied or adapted for other solids, as would be appreciated by one of ordinary skill in the art with the benefit of the present disclosure.

Moreover, for seawater (typically having relatively high sulfate concentration) as the source water, sulfate compounds may precipitate. For seawater utilized in combination with aquifer water or produced water as the source water, mineral cations in the aquifer water or produced water can form compounds with sulfate in the seawater. In implementations, aquifer water (and/or produced water) may be utilize with no seawater as the source water.

An embodiment is a method of treatment with scale inhibitor, including adding scale inhibitor to source water to give injection water, conveying the injection water in a surface conduit to an injection well for injection into an oil reservoir in a subterranean formation, pumping the injection water through a wellbore of the injection well into the oil reservoir, obtaining a sample of the injection water (including suspended solids), and analyzing the suspended solids via EDS, XRD, or XRF, or any combinations thereof. In implementations, the method includes analyzing the suspended solids via EDS. The analyzing of the suspended solids may include separating the suspended solids from the sample, drying the suspended solids as separated, and analyzing the suspended solids as separated and dried via EDS, XRD, or XRF, or any combinations thereof. Adding the scale inhibitor to the source water may involve adding the scale inhibitor to the source water in the surface conduit at an addition point along the surface conduit, and wherein the surface conduit upstream of the addition point conveys the source water. The method may include collecting deposited solids from an internal surface of the surface conduit downstream of the addition point, wherein analyzing the suspended solids more generally involves analyzing solids including the suspended solids and the deposited solids, wherein the analyzing includes EDS, XRD, or XRF, or any combinations thereof. In implementations, the source water includes aquifer water produced from a water supply well into the surface conduit, and wherein adding the scale inhibitor to the source water involves adding the scale inhibitor to the surface conduit to give the injection water conveyed in the surface conduit.

The method may include determining by the analyzing via the EDS, XRD, or XRF that that the suspended solids do not include calcium carbonate solids, and deeming that the treatment with the scale inhibitor as effective in response to determining that the suspended solids do not comprise calcium carbonate solids. The method may include determining via the analyzing that the suspended solids include calcium carbonate solids, and imaging the calcium carbonate solids. The imaging may include, for example, SEM that can be ESEM. The method may include determining via the imaging that the calcium carbonate solids do not include calcium carbonate solids formed in presence of the scale inhibitor, and deeming that the treatment with the scale inhibitor as effective in response to determining that the calcium carbonate solids do not comprise calcium carbonate solids formed in the presence of the scale inhibitor. The method may include determining via the imaging that the calcium carbonate solids comprise calcium carbonate solids formed in presence of the scale inhibitor. The method may include adding more of the scale inhibitor to the source water in response to determining that the calcium carbonate solids include calcium carbonate solids formed in presence of the scale inhibitor. The adding of the scale inhibitor to the source water may involve adding the scale inhibitor to the source water in the surface conduit at an addition point along the surface conduit, and wherein the surface conduit upstream of the addition point conveys the source water. The method may include increasing addition rate of the scale inhibitor to the source water in response to determining that the calcium carbonate solids include calcium carbonate solids formed in presence of the scale inhibitor. The adding of the scale inhibitor to the source water may include adding the scale inhibitor via a squeeze treatment with the scale inhibitor of a water supply well that provides the source water. The adding of the scale inhibitor to the source water may include adding the scale inhibitor via a backside treatment with the scale inhibitor to a water supply well that provides the source water.

Another embodiment is a method of treatment with scale inhibitor, including adding scale inhibitor to source water to give injection water for injection via an injection well into an oil reservoir having crude oil. The method includes obtaining a sample of the injection water (having suspended solids), analyzing the suspended solids via EDS, XRD, or XRF, or any combinations thereof, thereby identifying calcium carbonate solids of the suspended solids, and analyzing the calcium carbonate solids via imaging, thereby identifying at least some of the calcium carbonate solids as formed in presence of the scale inhibitor. The method may include increasing an amount of the scale inhibitor added to the source water in response to identifying at least some of the calcium carbonate solids as formed in the presence of the scale inhibitor. The method may include [1] conveying the injection water in a surface conduit to the injection well for injection into the oil reservoir in a subterranean formation (wherein the injection well includes a wellbore formed in the subterranean formation) and [2] injecting the injection water through the wellbore into the oil reservoir in the subterranean formation. In implementations, the analyzing of the suspended solids is by EDS. In implementations, the imaging of the calcium carbonate solids is by SEM or ESEM, or both. Lastly, the method may include providing, via a water supply well, aquifer water from an aquifer in a subterranean formation as the source water.

Yet another embodiment is a method of treatment with scale inhibitor, including adding scale inhibitor to source water to give injection water for injection via an injection well into an oil reservoir, and conveying the injection water in a surface conduit to the injection well for injection into the oil reservoir. The method includes obtaining a sample of the injection water (having suspended solids), analyzing the suspended solids via EDS, thereby identifying calcium carbonate solids of the suspended solids, and analyzing the calcium carbonate solids via scanning electron microscopy (SEM) or environmental scanning electron microscopy (ESEM), or both, thereby identifying at least some of the calcium carbonate solids as formed in presence of the scale inhibitor. The method includes increasing an amount of the scale inhibitor added to the source water in response to identifying at least some of the calcium carbonate solids as formed in the presence of the scale inhibitor. The method may include providing, via a water supply well, aquifer water from an aquifer in a subterranean formation as the source water into the surface conduit, and wherein adding the scale inhibitor to the source water includes adding the scale inhibitor to the surface conduit to give the injection water conveyed in the surface conduit.

A number of implementations have been described. Nevertheless, it will be understood that various modifications may be made without departing from the spirit and scope of the disclosure.

What is claimed is:

1. A method of treatment with scale inhibitor, comprising:
   adding scale inhibitor to source water to give injection water;
   conveying the injection water in a surface conduit to an injection well for injection into an oil reservoir in a subterranean formation;
   obtaining a sample of the injection water, wherein the sample of the injection water comprises suspended solids;
   analyzing the suspended solids via energy dispersive x-ray spectroscopy (EDS), x-ray diffraction (XRD), or x-ray fluorescence (XRF), or any combinations thereof; and
   pumping the injection water through a wellbore of the injection well into the oil reservoir.

2. The method of claim 1, comprising analyzing the suspended solids via EDS.

3. The method of claim 1, wherein analyzing the suspended solids comprises:
   separating the suspended solids from the sample;
   drying the suspended solids as separated; and
   analyzing the suspended solids as separated and dried via EDS, XRD, or XRF, or any combinations thereof.

4. The method of claim 1, wherein adding the scale inhibitor to the source water comprises adding the scale inhibitor to the source water in the surface conduit at an addition point along the surface conduit, and wherein the surface conduit upstream of the addition point conveys the source water.

5. The method of claim 4, comprising collecting deposited solids from an internal surface of the surface conduit downstream of the addition point, wherein analyzing the suspended solids comprises analyzing solids including the suspended solids and the deposited solids, wherein the analyzing comprises EDS, XRD, or XRF, or any combinations thereof.

6. The method of claim 1, wherein the source water comprises aquifer water produced from a water supply well into the surface conduit, and wherein adding the scale inhibitor to the source water comprises adding the scale inhibitor to the surface conduit to give the injection water conveyed in the surface conduit.

7. The method of claim 1, comprising:
   determining via the analyzing that that the suspended solids do not comprise calcium carbonate solids; and deeming that the treatment with the scale inhibitor as effective in response to determining that the suspended solids do not comprise calcium carbonate solids.

8. The method of claim 1, comprising:
   determining via the analyzing that the suspended solids comprise calcium carbonate solids; and
   imaging the calcium carbonate solids.

9. The method of claim 8, wherein the imaging comprises scanning electron microscopy (SEM).

10. The method of claim 9, wherein the SEM comprises environmental scanning electron microscopy (ESEM).

11. The method of claim 8, comprising:
   determining via the imaging that the calcium carbonate solids do not comprise calcium carbonate solids formed in presence of the scale inhibitor; and
   deeming that the treatment with the scale inhibitor as effective in response to determining that the calcium carbonate solids do not comprise calcium carbonate solids formed in the presence of the scale inhibitor.

12. The method of claim 8, comprising determining via the imaging that the calcium carbonate solids comprise calcium carbonate solids formed in presence of the scale inhibitor.

13. The method of claim 12, comprising adding more of the scale inhibitor to the source water in response to determining that the calcium carbonate solids comprise calcium carbonate solids formed in presence of the scale inhibitor.

14. The method of claim 12, wherein adding the scale inhibitor to the source water comprises adding the scale inhibitor to the source water in the surface conduit at an addition point along the surface conduit, and wherein the surface conduit upstream of the addition point conveys the source water.

15. The method of claim 14, comprising increasing addition rate of the scale inhibitor to the source water in response to determining that the calcium carbonate solids comprise calcium carbonate solids formed in presence of the scale inhibitor.

16. The method of claim 1, wherein adding the scale inhibitor to the source water comprises adding the scale inhibitor via a squeeze treatment with the scale inhibitor of a water supply well that provides the source water.

17. The method of claim 1, wherein adding the scale inhibitor to the source water comprises adding the scale inhibitor via a backside treatment with the scale inhibitor to a water supply well that provides the source water.

18. A method of treatment with scale inhibitor, comprising:
   adding scale inhibitor to source water to give injection water for injection via an injection well into an oil reservoir comprising crude oil;
   obtaining a sample of the injection water, wherein the sample of the injection water comprises suspended solids;
   analyzing the suspended solids via energy dispersive x-ray spectroscopy (EDS), x-ray diffraction (XRD), or x-ray fluorescence (XRF), or any combinations thereof, thereby identifying calcium carbonate solids of the suspended solids; and
   analyzing the calcium carbonate solids via imaging, thereby identifying at least some of the calcium carbonate solids as formed in presence of the scale inhibitor.

19. The method of claim 18, comprising increasing an amount of the scale inhibitor added to the source water in response to identifying at least some of the calcium carbonate solids as formed in the presence of the scale inhibitor.

20. The method of claim 18, comprising:
   conveying the injection water in a surface conduit to the injection well for injection into the oil reservoir in a subterranean formation, wherein the injection well comprises a wellbore formed in the subterranean formation; and
   injecting the injection water through the wellbore into the oil reservoir in the subterranean formation.

21. The method of claim 18, wherein analyzing the suspended solids comprises analyzing the suspended solids via EDS.

22. The method of claim 18, wherein the imaging comprises scanning electron microscopy (SEM) or environmental scanning electron microscopy (ESEM), or both.

23. The method of claim 18, comprising providing, via a water supply well, aquifer water from an aquifer in a subterranean formation as the source water.

24. A method of treatment with scale inhibitor, comprising:
   adding scale inhibitor to source water to give injection water for injection via an injection well into an oil reservoir;
   conveying the injection water in a surface conduit to the injection well for injection into the oil reservoir;
   obtaining a sample of the injection water, wherein the sample of the injection water comprises suspended solids;
   analyzing the suspended solids via energy dispersive x-ray spectroscopy (EDS), thereby identifying calcium carbonate solids of the suspended solids;
   analyzing the calcium carbonate solids via scanning electron microscopy (SEM) or environmental scanning electron microscopy (ESEM), or both, thereby identifying at least some of the calcium carbonate solids as formed in presence of the scale inhibitor; and
   increasing an amount of the scale inhibitor added to the source water in response to identifying at least some of the calcium carbonate solids as formed in the presence of the scale inhibitor.

25. The method of claim 24, comprising providing, via a water supply well, aquifer water from an aquifer in a subterranean formation as the source water into the surface conduit, and wherein adding the scale inhibitor to the source water comprises adding the scale inhibitor to the surface conduit to give the injection water conveyed in the surface conduit.

* * * * *